United States Patent [19]

Takahashi et al.

[11] Patent Number: 5,598,509
[45] Date of Patent: Jan. 28, 1997

[54] METHOD OF CONFIGURING A NEURAL NETWORK AND A DIAGNOSIS/RECOGNITION SYSTEM USING THE SAME

[75] Inventors: Isao Takahashi, Maebashi; Fumihiro Endo; Tokio Yamagiwa, both of Hitachi, all of Japan

[73] Assignee: Hitachi, Ltd., Tokyo, Japan

[21] Appl. No.: 214,769

[22] Filed: Mar. 18, 1994

Related U.S. Application Data

[63] Continuation-in-part of Ser. No. 111,472, Aug. 25, 1993.

[30] Foreign Application Priority Data

Aug. 28, 1992 [JP] Japan .................................. 4-230208
Aug. 31, 1992 [JP] Japan .................................. 4-230859
Mar. 18, 1993 [JP] Japan .................................. 5-058328

[51] Int. Cl.$^6$ ............................... G06E 1/00; G06E 3/00
[52] U.S. Cl. ............................. 395/22; 395/23; 382/157; 382/159
[58] Field of Search ......................... 395/22, 23; 382/14, 382/157, 159

[56] References Cited

U.S. PATENT DOCUMENTS

| | | | |
|---|---|---|---|
| 4,941,122 | 7/1990 | Weideman | 364/807 |
| 5,023,045 | 6/1991 | Watanabe et al. | 376/215 |
| 5,046,020 | 9/1991 | Filkin | 364/513 |
| 5,060,278 | 10/1991 | Fukumizu | 382/14 |
| 5,060,279 | 10/1991 | Crawford et al. | 382/14 |
| 5,091,864 | 2/1992 | Baji et al. | 395/27 |
| 5,119,468 | 6/1992 | Owens | 395/22 |
| 5,129,039 | 7/1992 | Hiraiwa | 395/24 |
| 5,146,541 | 9/1992 | Speidel | 395/24 |
| 5,155,801 | 10/1992 | Lincoln | 395/22 |
| 5,195,171 | 3/1993 | Takatori et al. | 395/24 |
| 5,222,194 | 6/1993 | Nishimura | 395/23 |
| 5,255,347 | 10/1993 | Matsuba et al. | 395/23 |
| 5,333,238 | 7/1994 | Fakazu et al. | 395/21 |

FOREIGN PATENT DOCUMENTS

| | | |
|---|---|---|
| 2-81161 | 3/1990 | Japan . |
| 2-170263 | 7/1990 | Japan . |
| 2-272326 | 11/1990 | Japan . |
| 2-296161 | 12/1990 | Japan . |
| 2-297074 | 12/1990 | Japan . |
| 3-201158 | 9/1991 | Japan . |
| 3-201160 | 9/1991 | Japan . |
| 3-210686 | 9/1991 | Japan . |
| 3-238370 | 10/1991 | Japan . |
| 3-250243 | 11/1991 | Japan . |
| 3-286388 | 12/1991 | Japan . |

OTHER PUBLICATIONS

"A Module Neural Network Application to GIS Preventive Maintenance System", H. Ogi et al, pp. 339–344.

"Development of the Detective and Diagnostic Techniques of Partial Discharge in GIS", M. Oyama, et al, pp. 321–326.

Speech Processing 2, Audio, Neural Networks, Underwater Acoustics, San Francisco, Mar. 23–26, 1992, vol. 2, 23 Mar. 1992 Institute of Electrical and Electronics Engineers, pp. 401–404, XP 000357022 RE R 'A Technique for Defining The Architecture and Weights of a Neural Image Classifier' p. 401, left column, line 1—p. 402, right column, line 54.

(List continued on next page.)

*Primary Examiner*—Robert W. Downs
*Assistant Examiner*—A. Katbab
*Attorney, Agent, or Firm*—Antonelli, Terry, Stout & Kraus

[57] ABSTRACT

In a recognition/diagnosis method, a relation between total sums of inputs of respective cases and teacher data is listed in the order of magnitude of the total sums of inputs. Based on the value of the teacher data for the input having the maximum total sum and the number of times of change of teacher data in the table are considered, a configuration of a neural network (the number of hidden layers and the number of neurons thereof) is determined. Coupling weights are analytically calculated based on the table.

18 Claims, 16 Drawing Sheets

OTHER PUBLICATIONS

Proceedings of the International Joint Conference on Neural Network, Singapore, Nov. 18–21, 1991, vol. 1 of 3, 18 Nov. 1991 Institute of Electrical and Electronics Engineers, pp. 813–820, XP 000325724 Chu Y C et al 'A Neural Network Which Learns Decision Boundaries with Nonlinear Clustering' p. 813, line 1—line 35.

IEEE Transactions on Neural Networks, vol. 2, No. 4, 1 Jul. 1991 pp. 467–471, XP 000228662 Sartori M A et al 'A Simple Method to Derive Bounds on the Size and to Train Multilayer Neural Networks'.

Proceedings of the International Joint Conference on Neural Network (IJCNN), Baltimore, Jun. 7–11, 1992, vol. 1, 7 Jun. 1992 Institute of Electrical and Electronics Engineers, pp. 676–681, XP 000340280 Davis D T et al 'Attentional Focus Training by Boundary Region Data Selection' p. 676, line 1—p. 677, line 22.

TOTAL SUM (a)

(b)

(c)

(d)

(e)

(f)

(g)

(h)

(i)

( EQUIVALENT COUPLING WEIGHT TO INPUT IS $K_iW_a$ )

F I G.20
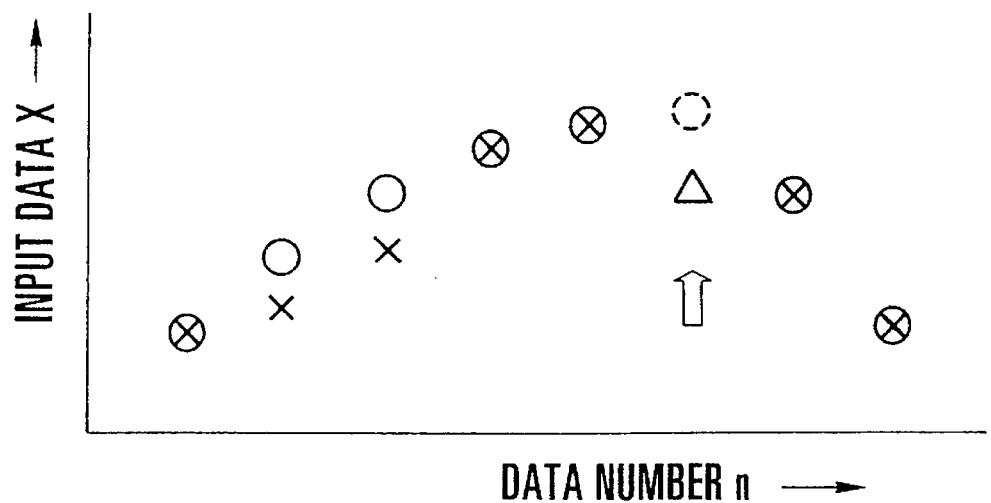
F I G.21
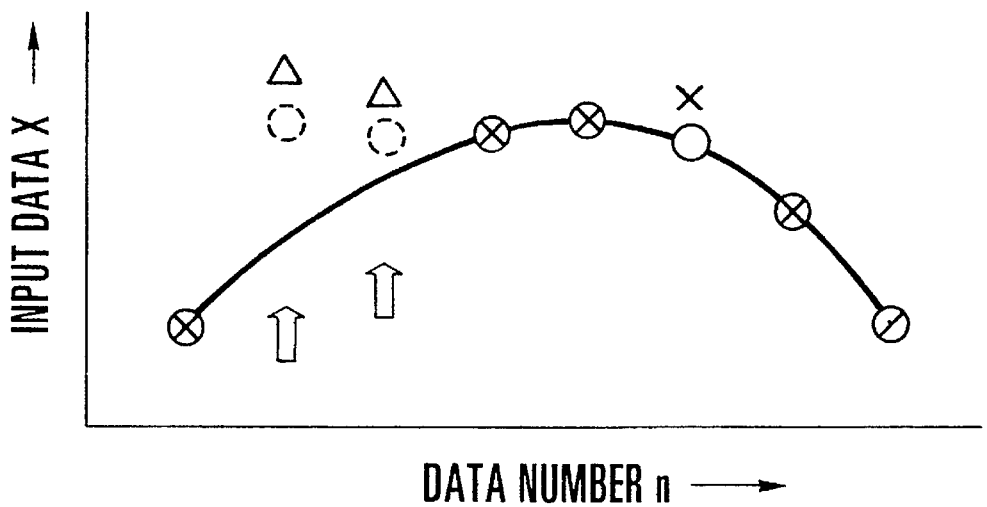

METHOD OF CONFIGURING A NEURAL NETWORK AND A DIAGNOSIS/RECOGNITION SYSTEM USING THE SAME

CROSS REFERENCE TO RELATED APPLICATION

This is a continuation-in-part application of U.S. patent application Ser. No. 08/111,472 filed Aug. 25, 1993. The disclosure of the above application is incorporated herein by reference.

BACKGROUND OF THE INVENTION

1. Field of the Invention

The present invention relates to a recognition or diagnosis method primarily using a neural network for diagnosing the presence or absence of a fault in a current operation status by utilizing past operation information of various components of a power supply circuit such as a gas insulated switchgear (GIS) or a transformer. It is applicable to not only various engineering fields but also the medical field, and more generally to the recognition and diagnosis of physical, chemical and biological phenomena.

2. Description of the Related Art

JP-A-2-297074, a diagnosis method utilizing a neural network is proposed. In the method, past status of various types of equipment are previously learned by a neural network having a multi-layer structure. When a new status of the equipment is input, whether the equipment is normal or not is determined based on the learned result. If they are determined to be abnormal, a cause therefor is inferred.

In JP-A-2-272326, detailed description is made regarding mechanical vibration, acoustic vibration and electric oscillation of a rotary machine.

In JP-A-2-100757, a learning method of a parallel neural network is proposed. It is stated therein that a back propagation method is becoming effective as a learning method. A conventional learning method has disadvantages in that the learning does not proceed once it falls in a local minimum and a precision of learning sharply decreases when the amount of data to be learned is excessively large. In the proposed method, more than one neural network is connected in parallel to serially learn in order to improve the efficiency and precision of the learning. Other art related to the present invention are disclosed in U.S. Pat. No. 5,023,045, JP-A-2-206721, JP-A-4-120479, JP-A-3-201079 and JP-A-3-092975.

FIG. 1 shows a conventional neural network. Any number (one in the illustrated example) of hidden layers is provided between an input layer and an output layer. A set of input data $X_1, X_2, X_3, \ldots, X_n$ are input to the input layer. In FIG. 1, "1" is also always supplied for adjusting the output from neurons. Products of those inputs and coupling weights $W_1, W_2, W_3, \ldots, W_n, W_{n+1}$ are inputs $U_1$ to a neuron Ne. An output from the neuron is $V_1$. $U_1$ and $V_1$ are calculated by equations (1) and (2).

$$U_1 = \sum_{i=1}^{n} X_i \cdot W_i + 1 \cdot W_{n+1} \quad (1)$$

$$V_1 = \frac{1}{(1 + e^{-U_1})} \quad (2)$$

Similar equations are applied to the inputs and the outputs of other neurons of the hidden layers and the output layers. Only one Na of the neurons of each hidden layer is coupled with "1" for adjusting the output of a neuron connected thereto which the output of the connected is equal to "1" to provide a predetermined coupling weight.

Thus, in the conventional neural network, an operation of learning is essential. The learning regards coupling weights among the neurons that are determined through iterative calculations so that a calculated value approximated to data called teacher data, which is predetermined for input data, is output from the output layer when the input data is applied. For example, learning is utilized to gradually modify the coupling weights through the iterative calculations, to thereby reduce an error which is defined as 0.5 times of a square sum of differences between the teacher data and the calculated output. If the learning proceeds well, the error decreases, but in some cases the error does not decrease and the calculated output is not attained with sufficient precision even after a large amount of learning iteration. Such a case is referred to as the neural network having fallen in a local minimum. In this case, it is not possible to get out of the local minimum whatever number of times of the learning is increased and therefore appropriate coupling weights are not determined.

Even if the calculated output converges to a desired value, a large amount of learning iterations requires a very long time (for example, several hours or more) depending on the scale of the neural network and the teacher data.

In the conventional neural network, the optimum number of hidden layers and the number of neurons are determined by a trial and error method. It is inefficient and improvement thereof has been desired.

SUMMARY OF THE INVENTION

It is an object of the present invention to provide a method having a high generalization ability to solve the above problems.

A method for analytically determining coupling weights of neurons from input data and teacher data has not been known but a method has been recently developed for analytically determining coupling weights of neurons, which is utilized in the present invention.

When the coupling weight is to be determined by iterative learning, the above method for analytically determining the coupling weights may be utilized. For example, the number of hidden layers, the number of neurons thereof and what is made clear relating to the coupling weight are partially utilized. The following means is further utilized.

(1) As will be described in detail hereinafter, characteristics of input data are examined from as wide a range as possible, and learning data is classified into several classes. Then, the proposed method is applied to each of the classes of learning data.

(2) A range of data scatter to be learned is considered and a corresponding design is made such that a correct solution is obtained if diagnosis data is within the range of data scatter.

(3) If a correct solution is determined after the diagnosis, the diagnosis data and the correct solution are made available as learning data and teacher data in the next run.

(4) In case of diagnosis, the inference is set logically more strict.

The present invention relates to a recognition or diagnosis method using a neural network having an input layer, a hidden layer and an output layer in which learning data input to the input layer are classified into a plurality of classes in accordance with characteristics of the data, the learning data are input for each class, a total sum is determined for each case, corresponding teacher data and the total sum are associated in the order of magnitude for each output of the output layer, and coupling weights are determined based on the teacher data corresponding to the case having a maximum total sum in the above table, the total sums before and after the change of the teacher data and the teacher data.

The present invention further relates to a recognition or diagnosis method using a neural network having an input layer, a hidden layer and an output layer in which input data is input for each value for each case based on an upper limit and a lower limit of the input data for each case input to the input layer, a total sum is determined for each case, corresponding teacher data and the total sum are associated in the order of magnitude for each output of the output layer, and the coupling weight is determined based on the teacher data corresponding to the case having a maximum total sum in the above table, the total sums before and after the change of the teacher data and the teacher data.

The input data input to the input layer preferably has the same coupling weight multiplied to the upper limit and the lower limit.

The present invention further relates to a recognition or diagnosis method using a neural network having an input layer, a hidden layer and an output layer in which an input sum is determined by selecting coupling weights such that the input sum determined from a case other than a particular case input to the input layer does not fall between two input sums determined from an upper limit and a lower limit of the input data of the particular case, the input sum is input as the input data, an input total sum is determined for each case, corresponding teacher data and the input total sums are associated in the order of magnitude for each output of the output layer, and the coupling weight is determined based on the teacher data corresponding to the case having the maximum input total sum in the above table, the input total sums before and after the change of the teacher data and the teacher data.

The teacher data of the particular case and the teacher data of the case other than the particular case are preferably different from each other.

Preferably, the coupling weight is selected such that the second hidden layer functions as an AND circuit and the output layer functions as an OR circuit when there are two hidden layers and the teacher data corresponding to the case having the maximum total sum is 0. When there are two hidden layers and the teacher data corresponding to the case having the maximum total sum is 1, it is preferable to select the coupling weight such that the second hidden layer functions as an OR circuit and the output layer functions as an AND circuit.

Further, the input data is preferably a reciprocal for each case so that the magnitude relation of the input data is reversed.

Preferably, a back propagation iterative learning method is used to calculate the coupling weights which are principal parts of the neural network.

The present invention further relates to a recognition or diagnosis method using a neural network having an input layer, a hidden layer and an output layer in which learning data is input to the input layer for each case, a total sum is calculated for each case, corresponding teacher data and the total sum are associated in the order of magnitude for each output of the output layer, a coupling weight is determined based on the teacher data corresponding to the case having a maximum total sum in the above table, the total sums before and after the change of the teacher data and the teacher data, and the fact that the input diagnosis data is out of the range of scatter designated for the leaning data is displayed.

Preferably, the teacher data and the total sums are listed in the order of magnitude to associate the teacher data with the total sums in the order of magnitude.

The present invention further relates to a recognition or diagnosis method using a neural network having an input layer, a hidden layer and an output layer in which when diagnosis data is to be input and a correct solution to the diagnosis data is known, the diagnosis data and the corresponding correct solution are transferred as a part of learning data after the diagnosis.

The present invention further relates to a recognition or diagnosis method using a neural network having an input layer, a hidden layer and an output layer in which an output to diagnosis data is calculated after the diagnosis data has been input, at least one probable learning data is inferred from the output, the learning data is compared with the diagnosis data, and a result is displayed.

Where the inferred learning data has a range of scatter, it is preferable to compare the diagnosis data with the learning data having the range of scatter and display a result.

Preferably, the first coupling weight to be multiplied to the input data of the input layer is different from other coupling weights.

Further, in accordance with the present invention, the diagnosis data and the learning data are directly compared; whether the diagnosis data and the learning data of a particular case totally match, partially match or totally mismatch is determined, a result is displayed; the diagnosis data and the learning data having a range of scatter are directly compared; whether the diagnosis data is totally in the range, partially in the range or totally not in the range is determined; and a result is displayed.

Further, in accordance with the present invention, simultaneous equations are prepared by using a calculation formula for the input to the neuron based on an upper limit and a lower limit of the input data having a range of scatter, the simultaneous equations are solved to determine a coefficient, and the neural network is utilized based on the coupling weight.

Further, the present invention relates to a recognition or diagnosis method using a neural network having an input layer, a hidden layer and an output layer weighted by coupling weights which has a capability to evaluate teacher data for determining the coupling weights.

Further, in accordance with the present invention, a system has an electrical circuit to be used under a plurality of conditions and the circuit is diagnosed by using a neural network. The plurality of conditions are taken as learning data to determine coupling weights of the neural network.

The present invention is summarized as follows. A threshold modifying neuron which always outputs "1" is provided for each layer except the output layer, a total sum of inputs is calculated for each case, total sums are listed together with corresponding teacher data in the order of magnitude of the total sum, neurons equal to the number of times of change of the teacher data are sequentially arranged as a first hidden layer based on the number N of times of change of the teacher data in the list, and where N is odd, $(N-1)/2$ neurons are arranged as a second hidden layer, outputs of the first hidden layer are sequentially input to the second hidden layer two at a time, outputs thereof are input to the output layer together with the reaming one output of the first hidden layer. Where N is even, N/2 neurons are arranged, the outputs of the first hidden layer are sequentially input two at a time, the outputs thereof are input to the output layer, and the coupling weights are analytically determined based on the teacher data corresponding the case having a maximum input sum of the table and the input sums before and after the change of the teacher data and the teacher data.

Preferably, any numbers $K_i$, which are not all equal, for example, a random number, are multiplied to the inputs before summation instead of simple summation of the inputs for each case.

Further, it is preferable to provide one threshold modifying neuron which always outputs "1" for each layer except the output layer and a total sum of products of the inputs and appropriate coupling weights is determined for each case.

Further, input sums which are products of an upper limit and a lower limit of the input and an appropriate same coupling weight are prepared for the input data of each case based on the upper limit and the lower limit of the scatter of the input data of each case, and the coupling weights are selected such that the input sum determined from other cases does not fall between two input sums determined based on the upper limit and the lower limit of the inputs of a particular case. Namely, the weights are determined such that the sum of other case does not fall in the range of the first determined case.

Further, input sums which are products of an upper limit and a lower limit of the input and an appropriate same coupling weight are prepared for the input data of each case based on the upper limit and the lower limit of the scatter of the input data of each case, and the coupling weights are selected such that the input sum determined from other cases having teacher data other than the teacher data of a particular case does not fall between two input sums determined based on the upper limit and the lower limit of the inputs of the particular case.

Further, the fact of diagnosis is preferably indicated by any means such as a display screen of video display means or by alarm sound.

The diagnosis data and the learning data are preferably compared for total match, partial match or total mismatch, and a function to classify the result is preferably provided.

A matrix is preferably used as means for comparing data numbers of the diagnosis data and the learning data.

(1) By the use of the analytical approach, the iterative learning required in the prior art is not necessary. An optimum number of hidden layers of the neural network and the number of neurons can be predetermined. No problem of local minimum arises. Accordingly, the time from the input of data to the diagnosis utilizing the neural network can be reduced. Since the present method may be applicable irrespective of the number of input data or the number of cases, the coupling weights among the neurons in a large scale neural network can be exactly determined in a short time.

(2) By using the iterative learning together with the analytical approach, the significant reduction of the learning time is attained.

(3) Since the number of times of calculation is significantly reduced. The recognition or diagnosis may be implemented in an economical notebook type personal computer depending on a memory capacity thereof.

(4) Based on data of a particular form after the classification, the number of cases to be compared for the similarity is smaller after the classification and the comparison is facilitated and the precision of diagnosis is naturally improved.

(5) Since data in the appropriate range of scatter is accepted as a correct solution, the precision of diagnosis to unlearned data is naturally improved.

(6) When a result of diagnosis is prepared and if it is a correct solution, the diagnosis data and the correct solution are taken as the learning data for the next run. Accordingly, the precision of diagnosis is naturally improved gradually.

(7) By effecting the diagnosis logically more strict, the precision of diagnosis is further improved.

BRIEF DESCRIPTION OF THE DRAWINGS

FIG. 20 shows a method (No. 1) in which some data is used by reciprocals;

FIG. 21 shows a method (No. 2) in which some data is used by reciprocals;

DESCRIPTION OF THE PREFERRED EMBODIMENTS

A diagnosis/control neural network system 1 of the present invention is now explained in detail with reference to the accompanying drawings.

Figure 3:
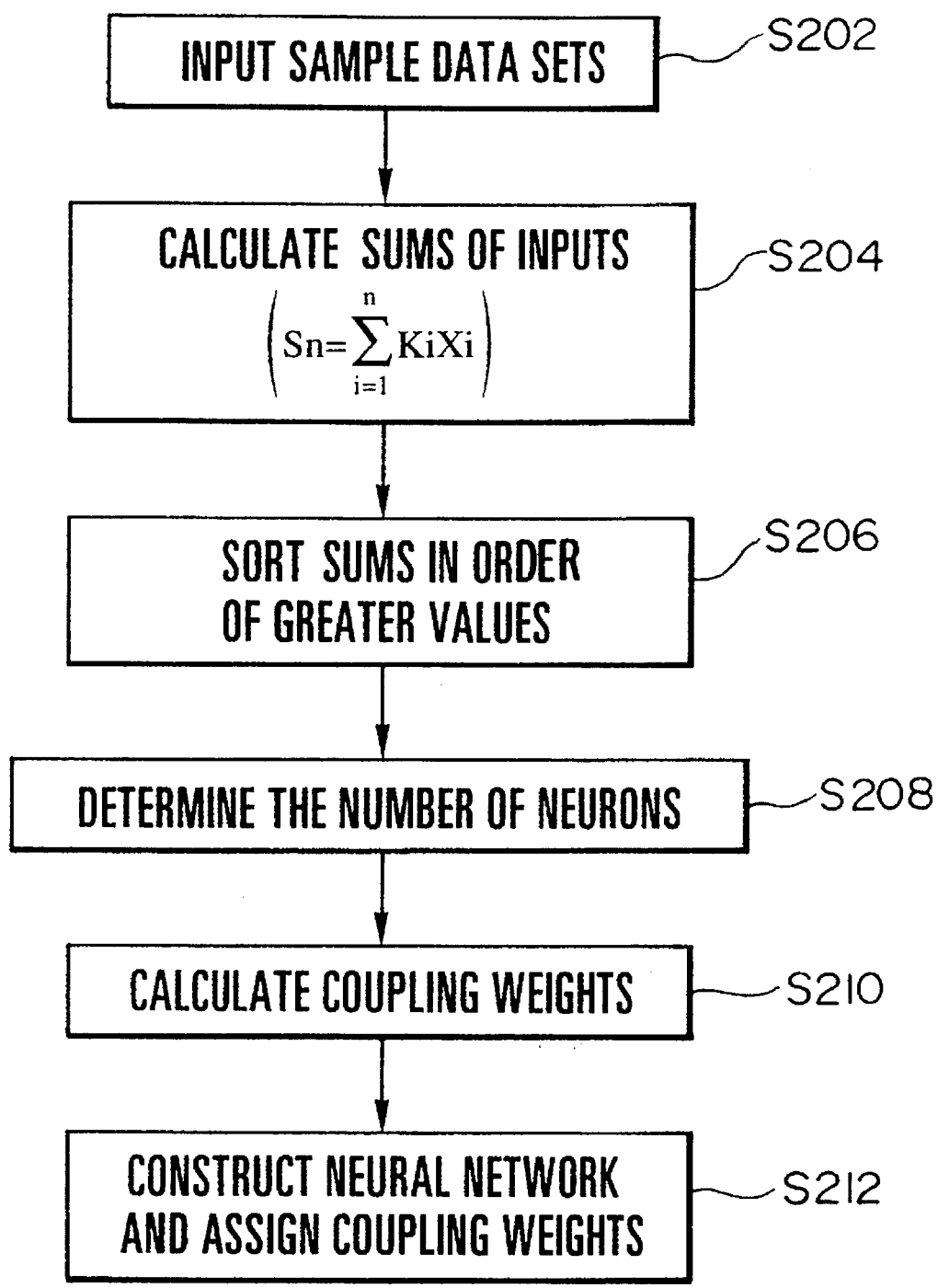
FIG. 3 shows a flow chart of an operation of a network configuring unit shown in FIG. 2.

First, a method for configuring the neural network of the present invention is now explained with reference to FIG. 3.

In step S202, the sample data sets and teacher data set for the respective cases are input. The sample data of each set for the case $X_i$ (i=1 to n) is any value of $0 \leq X_i \leq 1$, and the teacher data for the case is either "0" or "1". It has been found out that coupling weights $W_1, W_2, W_3, \ldots, W_n$ may be assumed to be equal to each other as shown by the following equation (3) in most cases although there is a very rare exception (which will be discussed hereinlater).

$$W_1 = W_2 = W_3 \ldots = W_n \quad (3)$$

A weight $W_{n+1}$ for a threshold modification input "1" usually assumes another value.

Taking the equation (3) into account, in the equation (1), a sum $\Sigma X_i$ of the input sample data $X_i$ is first calculated and then a coupling weight may be multiplied thereto. In step S204, a sum of the inputs is calculated for each data set corresponding to each case. In step S206, the sums are rearranged in an order of the total sum $\Sigma X_i$ and they are displayed together with the corresponding teacher data.

TABLE 1

| Case Number | $\Sigma X_i$ | Teacher Data |
|---|---|---|
| 1' | $S_1$ | 0 |
| 2' | $S_2$ | 1 |
| 3' | $S_3$ | . |
| . | . | . |
| n' | $S_n$ | . |

After the rearrangement, the number of neurons is determined in step S208, and the coupling weights to the neurons are calculated in step S210. Then, the coupling weight are set in the neural network unit in a step S212. It has been found thorough various considerations that the treatment in determining the coupling weights should be changed depending on whether the teacher data to the maximum total sum (which is designated by $S_1$) is "0" or "1". First, it is assumed that the teacher data for $S_1$ is "0".

For the convenience of explanation, a simple case will be discussed first.

Figure 4:
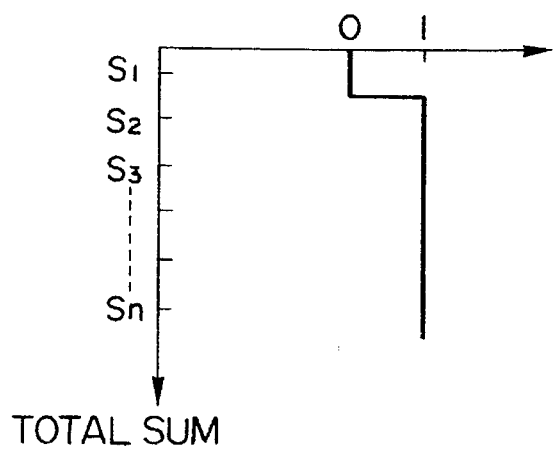
FIG. 4 shows a relation between sums of input data in the respective cases and teacher data in which the teachers data changes once.
Figure 5:
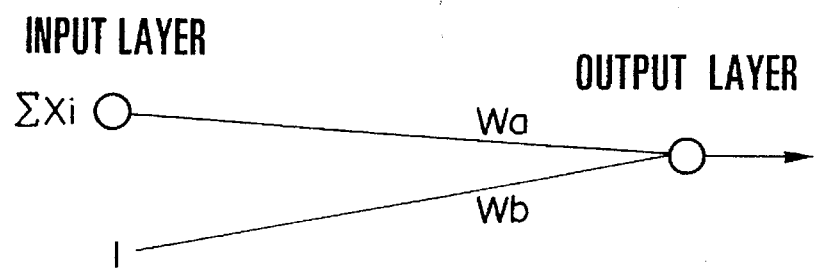
FIG. 5 shows a configuration of the neural network of the present invention when the teacher data changes once.

In FIG. 4, an ordinate represents $S_1, S_2, S_3, \ldots, S_n$ of Table 1 and an abscissa represents "0" and "1" of the teacher data. In FIG. 4, the teacher data changes from "0" to "1" at a boundary of $S_1$ and $S_2$. (It may change at another point). In the case of such a simple change, a hidden layer of the neural network is not necessary at all and the network can be configured simply as shown in FIG. 5. Coupling weights $W_a$ and $W_b$ of the neural network are determined in the following manner.

Looking at the change of the teacher data in Table 1, the sums of the inputs immediately before and after the boundary at which the teacher data changes as shown in Table 1, that is, $S_1$ and $S_2$ in the present example, are used to form the following linear simultaneous equations (4) and (5) with two unknowns.

$$S_1 \cdot W_a + 1 \cdot W_b = -10 \quad (4)$$

$$S_2 \cdot W_a + 1 \cdot W_b = 10 \quad (5)$$

The left terms represent inputs in the cases 1' and 2', and the right terms are the values of the inputs with which the output calculated by the formula (2) is practically "0" or "1" (Where $U_j = -10$, $1/(1+\exp(-(10))) \approx 0$, and where $U_j = 10$, $1/(\exp(-(10))) \approx 1$.).

Assuming $S_1 - S_2 \approx 0$, the above simultaneous equations are solved.

$$W_a = -20/(S_1 - S_2) \quad (6)$$

$$W_b = 10 + 20S_2/(S_1 - S_2) \quad (7)$$

Since $S_1 > S_2$, $W_a$ is negative and $W_b$ is positive. If S' is smaller than $S_2$, the following inequality is met.

$$S' \cdot W_a + 1 \cdot W_b > 10 \quad (8)$$

Thus, the outputs of $S_3$ et seq in FIG. 4 are closer to "1" than $S_2$ and they can be practically assumed to be "1". It is seen that a set of simultaneous equations as shown by (4) and (5) are for one change in the teacher data.

As seen from FIG. 5, the coupling weights $W_a$ and $W_b$ are uniquely determined as the solutions of the simultaneous equations. $\Sigma X_i$ is a variable but "1" is a fixed value. Where a sigmoid function is used as an output function of the neuron, a portion relating to "1" may be deleted from the circuit of FIG. 5 if a sigmoid function having an offset of $(1 \cdot W_b)$ along the abscissa is used.

Figure 6:
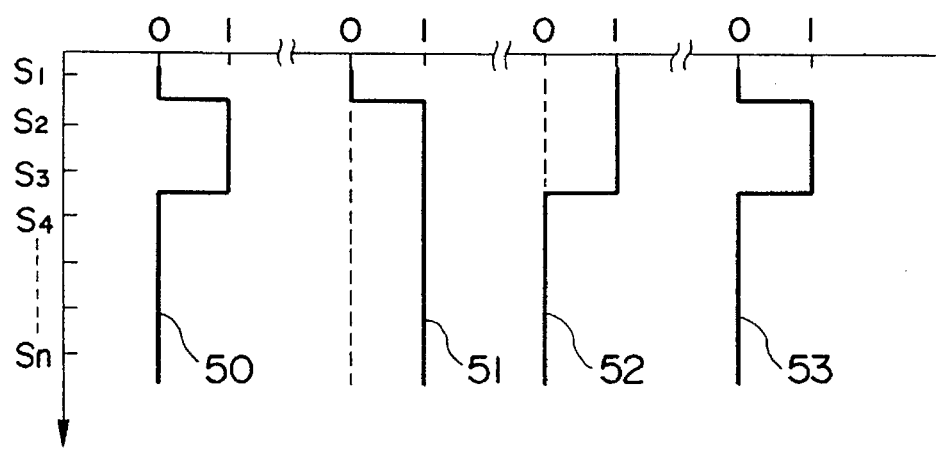
FIG. 6 shows a relation between total sums of input data in the respective cases and the teacher data in which the teacher data changes twice and a merging method therefor.
Figure 7:
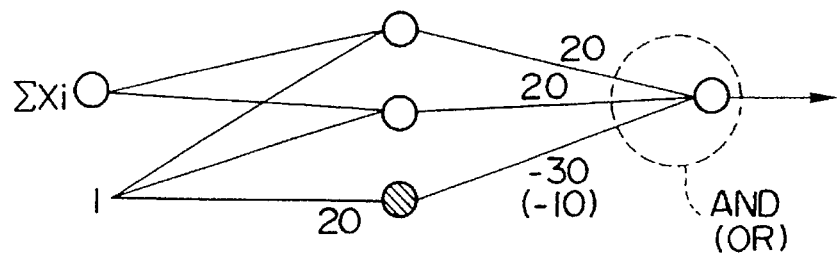
FIG. 7 shows a configuration of the neural network of the present invention when the teacher data changes twice.

Consider a case where the teacher data starts from "0", goes to "1" and returns to "0" again as shown by a segment 50 of FIG. 6. The teacher data changes two times. Since segments 51 and 52 can be generated in substantially the same manner as that in FIG. 4, they are combined to generate the segment 50. Since the output is "1" only when both of the segments 51 and 52 are "1", it is seen that they may be connected in an AND manner. The output of the AND circuit is "1" when both inputs are "1" so that a segment 53 is generated, which matches the segment 50. A neural network for this case is shown in FIG. 7. Coupling weights of the input layer and the hidden layer are derived by solving simultaneous equations similar to the equations (4) and (5) at the two changes of the teacher data. In this case, consideration is made for the case where the teacher data changes from "0" to "1", and the case where it subsequently changes from "1" to "0". The neuron shown by hatching at the bottom of the hidden layer is for threshold modification. When "20" is designated as the coupling weight between the input layer and the hidden layer as shown, the output is always practically "1". The coupling weights between the hidden layer and the output layer in an AND manner can be determined in a similar simple way. For example, they may be "20", "20" and "−30" as shown in FIG. 7. 20+20−30=+10 and 20−30=−10, which correspond to "+1" and "0", respectively. As seen, "−30" is a bias unit. An OR and (−10) shown in FIG. 7 will be explained hereinlater.

Figure 8:
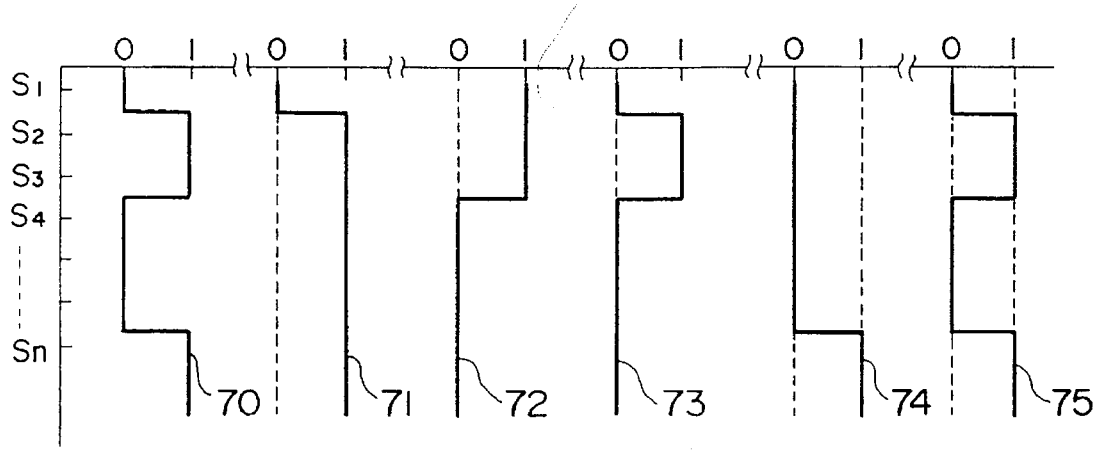
FIG. 8 shows a relation between total sums of input data in the respective cases and the teacher data in which the teacher data changes three times and a merging method therefor.

Consider a case where the teacher data changes three times as shown by a segment 70 of FIG. 8. Since segments 71 and 72 are generated in a similar manner to that described above, a segment 73 may be generated by ANDing them. A segment 74 is generated in a similar manner to that for the segment 71 and the segments 73 and 74 are coupled in an OR manner which outputs "1" when at least one of the inputs thereto is "1". In this manner, a segment 75 is generated. It matches the segment 70.

Figure 9:
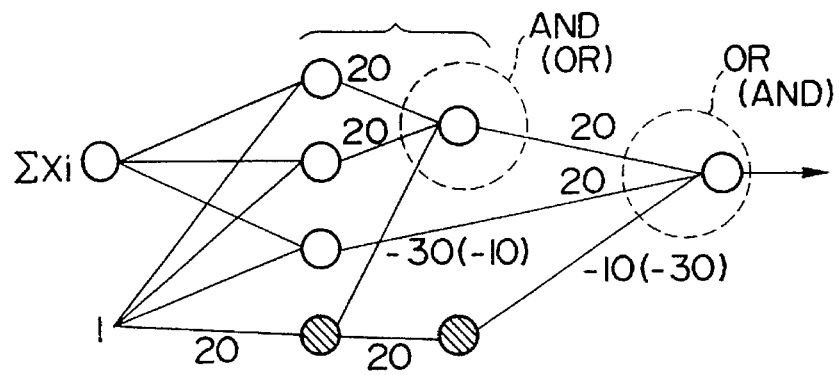
FIG. 9 shows a configuration of the neural network of the present invention when the teacher data changes three times; network of the present invention when the teacher data

A neural network therefor is shown in FIG. 9. Again, the neuron shown by hatching at the bottom of the hidden layer is a bias unit and it always outputs "1". Third output from the top of the first hidden layer is directly connected to the output layer without routing the AND operation neuron. The coupling weights of the OR operation neuron can be determined in a similar manner to that described above. They may be "20", "20" and "−10" as shown in FIG. 9 so that "1" is output when at least one of the inputs to the output layer is "1". (−10) is a bias unit. (OR) and (−10) of the hidden layer and (AND) and (−30) of the output layer shown in FIG. 9 will be explained hereinlater.

Similar analysis is conducted while the number of times of change of the teacher data is incremented to derive Table 2.

TABLE 2

The number of times of change of teacher data and the number of neurons of hidden layer

| | | | | | | | | |
|---|---|---|---|---|---|---|---|---|
| Number ($n_1$) of times of change of teacher data | 1 | 2 | 3 | 4 | 5 | 6 | 7 | $n_1$ |
| Number ($n_2$) of neurons of first hidden layer | (1) | 2 | 3 | 4 | 5 | 6 | 7 | $n_1$ |
| Number ($n_3$) of AND operation neurons of second hidden layer | 0 | (1) | 1 | 2 | 2 | 3 | 3 | $*_1$ |
| Number ($n_4$) of OR operation neurons of output layer | 0 | 0 | 1 | 1 | 1 | 1 | 1 | 1 |

$*_1$:
$$n_3 = \frac{n_1}{2} - \frac{1}{4}\{1 - (-1)^{n_1}\}$$

Table 2 shows a relation between the number of times of change of the teacher data and the number of neurons of the hidden layer. The number $n_2$ of neurons of the first hidden layer, the number $n_3$ of AND operation neurons (circuits) which are the second hidden layer, and the number $n_4$ of OR operation neurons (circuits) which are the output layer are shown for the numbers "1" to "7" of times of change of the teacher data and a general number $n_1$ (The neuron for modifying the threshold is separately provided for the hidden layer.). As shown in Table 2, the number of neurons in the first hidden layer is equal to the number $n_1$ of times of change of the teacher data. Where the number $n_1$ of times of change of the teacher data is "1", the neuron of the first hidden layer is the neuron of the output layer itself, and where the number $n_1$ of times of change of the teacher data is "2", the neurons of the second hidden layer are the neurons of the output layer. It is convenient to consider that they are the neurons of the hidden layer for the number "1" in the parentheses of Table 2 than to express it as no hidden layer, when a method for calculating the coupling weight is to be considered. It has been proved by the analysis that it is sufficient to consider two hidden layers at most. As described above, when there are a plurality of outputs from the output layer, the above calculation method is repeated.

Figure 1:
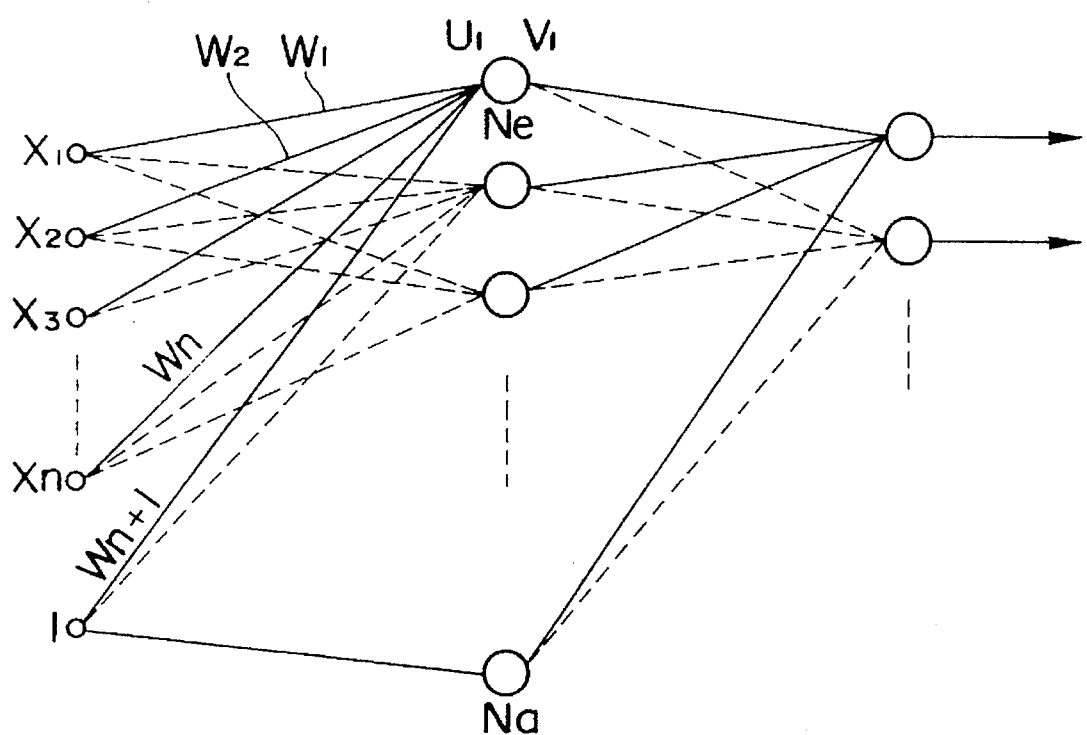
FIG. 1 shows a configuration of a conventional neural network.
Figure 2:
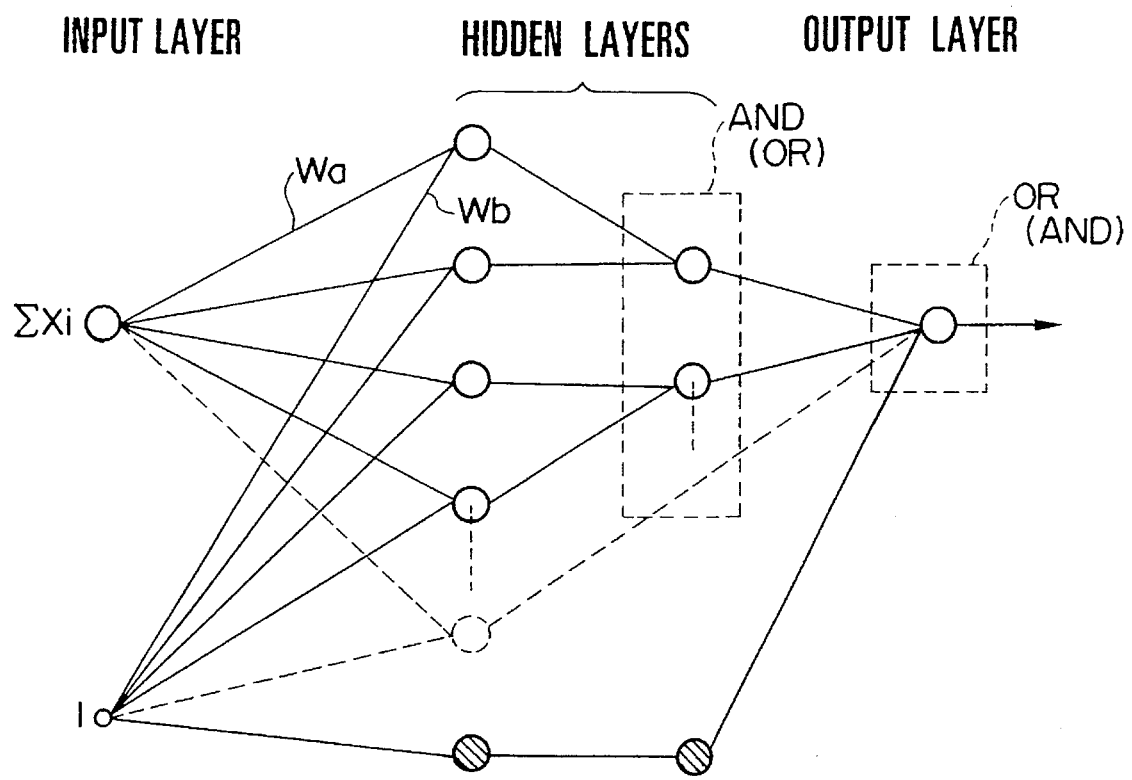
FIG. 2 shows a configuration of the neural network in accordance with an embodiment of the present invention.

More generally, where the number of times of change of the teacher data is relatively large, the configuration of the neural network of the present invention is one shown in FIG. 2. Where the number of times of change of the teacher data is odd, there is a direct connection from the first hidden layer to the output layer without routing the second hidden layer. The coupling weights are determined in the manner described above.

Consider a case where the teacher data corresponding to the maximum sum $S_1$ of the inputs is "1" as shown in Table 3.

TABLE 3

| Case Number | $\Sigma X_i$ | Teacher Data |
|---|---|---|
| 1' | $S_1$ | 1 |
| 2' | $S_2$ | 0 |
| 3' | $S_3$ | . |
| . | . | . |
| n' | $S_n$ | . |

Figure 10:
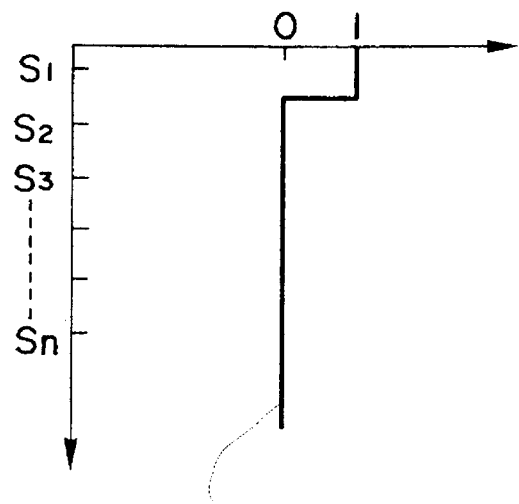
FIG. 10 shows other relation between total sums of input data in the respective cases and teacher data in which the teacher data changes once.

FIG. 10 shows a case where the teacher data changes once. In FIG. 10, the teacher data changes between $S_1$ and $S_2$ although it may change at another point. The neural network in this case requires no hidden layer and it may be the same one as that shown in FIG. 5 but the coupling weights are different, which are determined by simultaneous equations similar to the equations (4) and (5) but the sign of the right term is changed to render the outputs to be "1" and "0".

Figure 11:
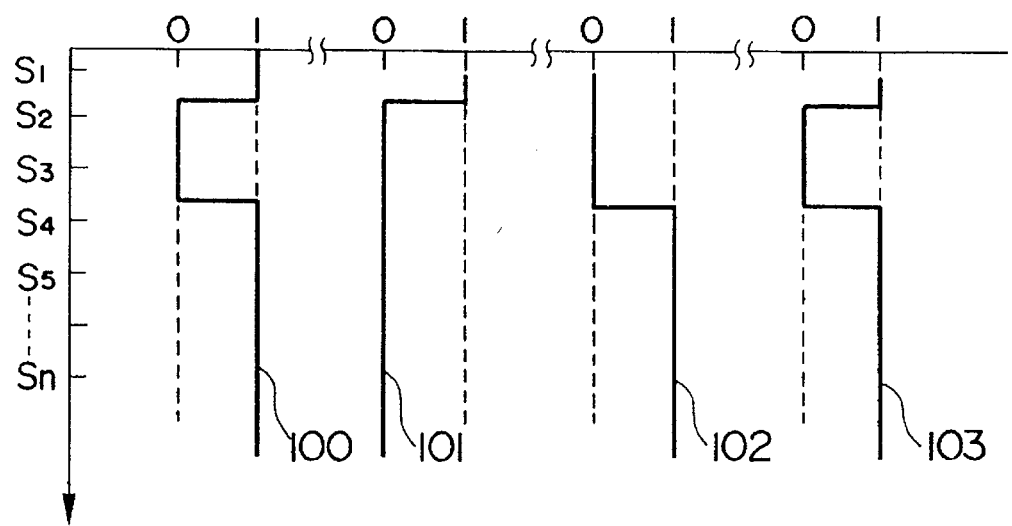
FIG. 11 shows another relation between total sums of input data in the respective cases and the teacher data in which the teacher data changes twice and a merging method therefor.

FIG. 11 shows a case where the teacher data changes twice as shown by a segment 100. Since segments 101 and 102 are generated in the same manner as that described above, the segment 100 may be generated based thereon. When at least one of the segments 101 and 102 is "1", the output is to be "1". That is, they are coupled in an OR manner. In this case, the neural network is substantially identical to that of FIG. 7 but the output layer functions as the OR operation instead of the AND operation and the coupling weight for the threshold modification is changed from "−30" to "−10", for example.

Figure 12:
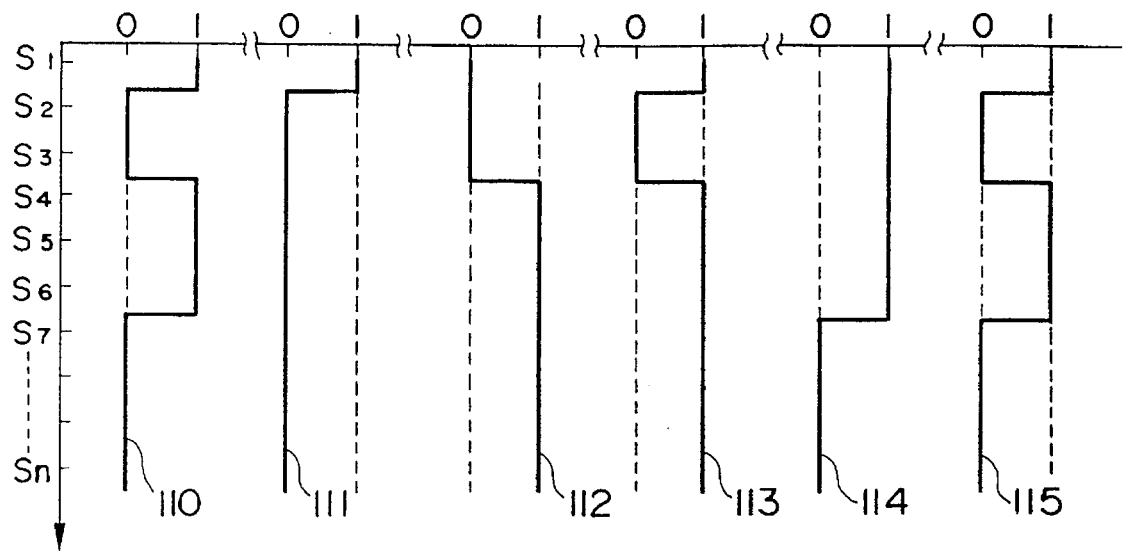
FIG. 12 shows another relation between total sums of input data in the respective cases and the teacher data in which the teacher data changes three times and a merging method therefor.
Figure 13:
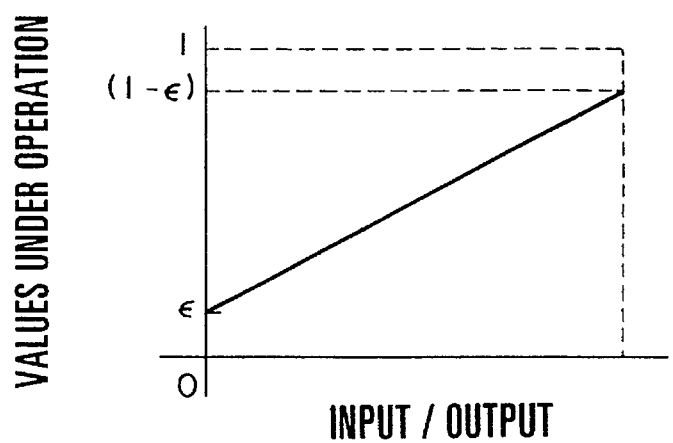
FIG. 13 shows conversion between values being operated and the input and output.

FIG. 12 shows a case where the teacher data changes three times as shown by a segment 110. In this case, segments 111 and 112 are generated in the same manner as that described above, and they are ORed to generate a segment 113. Then, a segment 114 is generated in the same manner as that for the segment 111. Finally, the segment 113 and the segment 114 are coupled in an AND manner to generate a segment 115, which matches the segment 110. In this case, the neural network is substantially identical to that of FIG. 9 but the OR operation neuron is arranged in the second hidden layer and the coupling weight for modifying the threshold is changed so that the output layer functions as the AND operation. The result of the analysis while incrementing the number of time of change of the teacher data is summarized in Table 4.

TABLE 4

| Number ($n_5$) of times of change of teacher data | 1 | 2 | 3 | 4 | 5 | 6 | 7 | $n_5$ |
|---|---|---|---|---|---|---|---|---|
| Number ($n_6$) of neurons in first hidden layer | (1) | 2 | 3 | 4 | 5 | 6 | 7 | $n_5$ |
| Number ($n_7$) if OR operation neurons of second hidden layer | 0 | (1) | 1 | 2 | 2 | 3 | 3 | $*_2$ |
| Number ($n_8$) of AND operation neurons of output layer | 0 | 0 | 1 | 1 | 1 | 1 | 1 | 1 |

$*_2$:

$$n_7 = \frac{n_5}{2} - \frac{1}{4}\{1-(-1)^{n_5}\}$$

Table 4 shows the number $n_6$ of the neurons of the first hidden layer, the number $n_7$ of OR operation neurons as the number of neurons of the second hidden layer, and the number $n_8$ of the AND operation neurons in the output layer, for the numbers "1" to "7" of times of change of the teacher data and a general number $n_5$ when the teacher data of $S_1$ is "1". As in Table 2, the neuron for modifying the threshold is separately provided for the hidden layer and the number "1" in the parentheses also represents the outputs of the output layer. By comparing Table 2 and Table 4, it is seen that the AND and OR are simply replaced. In this case, two hidden layers at most may be considered.

More generally, where the number of times of change of the teacher data is relatively large, the configuration of the neural network is like that shown in FIG. 2. When the number of times of change of the teacher data is odd, there is a case where direct connection is made from the first hidden layer to the output layer without routing the second hidden layer as shown by a broken line. The second hidden layer includes the OR operation neurons and the output layer includes the AND operation neurons. The method for calculating the coupling weights is the same as that described above.

Where a plurality of outputs are required for the output layer, the analysis is repeated for each output in the process described above. When the outputs are to be determined, a portion of the neural network may be shared if the boundary of the change of the teacher data shown in Table 1 and Table 2 are the same. Thus, the entire configuration may be simplified by utilizing this fact.

In the equations (6) and (7), when $S_1$ and $S_2$ are equal, the denominators of those equations are zero. In such a case, instead of simply summing the inputs, a number $K_i$ which is determined from a random number and which is not "1" is multiplied to each input before the summation. Namely, $\Sigma K_i X_i$ are calculated and then they are handled in the same manner as $S_1, S_2, S_3, \ldots, S_n$ of Table 1 and Table 3. By doing so, it rarely occurs that the denominators of the equations (6) and (7) are zero, except when the inputs of the plurality of cases are totally equal. If the denominators of the equations (6) and (7) are still zero, a process of deriving another random number may be repeated. As is apparent from the previous description, the fact that the denominator is zero causes a problem only when $S_1$ and $S_2$ are equal and the corresponding teacher data are different. Even if $S_1$ and $S_2$ are equal, no problem is raised if the corresponding teacher data are equal, since they are not used for the calculation of the coupling weights. Accordingly, more generally, in table 2 and Table 4, $\Sigma X_i$ is not calculated as a simple summation but $\Sigma K_i X_i$ is calculated by using the number $K_i$ determined from the random number and the calculation may be proceeded in the manner described above. In this case, the coupling weight for each input $X_i$ may be considered to be $K_i X_i$. When $K_i$ is used as the weight factor, it can be readily attained by adding a neuron to the input layer. It is assumed that $S_1'$ and $S_3'$ are equal, the corresponding teacher data are equal, and there is a sum $S_2'$ which is between $S_1'$ and $S_3'$ and has the teacher data equal to the teacher data for $S_1'$ and $S_3'$. In such a case, as is apparent from the above equations, there is no change among the three teacher data and hence $S_2'$ is not used for the calculation of the coupling weight. Accordingly, it is seen that the data $S_2'$ does not exist as the diagnosis data and it is not worth adding. It may be deleted to save the memory space. If the newly added teacher data changes the boundary of the change of the teacher data, it is worth adding.

In accordance with the present method, the following advantages are offered:

(1) The iterative leaning required in the prior art is not necessary.

(2) Since the number of hidden layers, the number of neurons required therefor and the coupling weights can be analytically determined, highly efficient diagnosis is attained in a short time.

(3) It has been proved that the number of hidden layers may be two at maximum.

(4) Since the coupling weights are analytically determined in a simple manner, it is applicable to a large scale system having a number of input data and output data.

(5) Since the iterative learning required in the prior art is not necessary, more economical computer may be used for the recognition and diagnosis.

(6) When the input data is to be added to enhance the precision of diagnosis, it can be determined whether or not it is worth adding based on the input data and the teacher data and if it is not worth adding, the addition is stopped. Accordingly, the memory can be efficiently used.

In the equations (4) and (5), the output "0" or "1" is approximated from the neuron. In a conversion shown in FIG. 14, considering $\epsilon$, a positive number close to zero, $\epsilon$ and $(1-\epsilon)$ are used for the intermediate calculation instead of "0" and "1", and in a final output stage, it is returned to a number in the range from "0" to "1". When this is applied to the right terms of the equations (4) and (5), they are expressed by $$S_1 \cdot W_a + 1 \cdot W_b = \log(\epsilon/(1-\epsilon)) \quad (9)$$

$$S_2 \cdot W_a + 1 \cdot W_b = -\log(\epsilon/(1-\epsilon)) \quad (10)$$

where log is natural logarithm. In the method in which the output of the equation (2) is treated as "0" or "1" for practical reasons, approximation calculation is partially included and hence an error is introduced. The present method includes no such error.

Figure 14A:
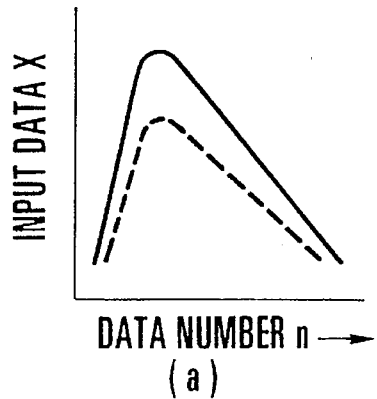
FIGS. 14A to 14I show classification of learning data.
Figure 14B:
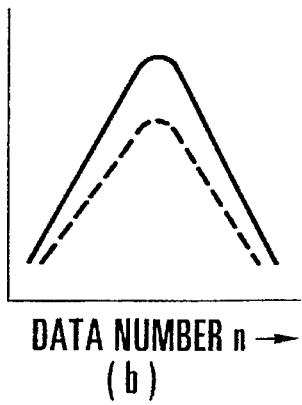
Figure 14C:
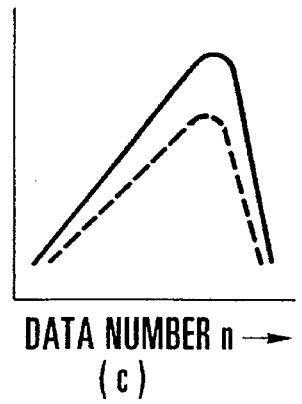
Figure 14D:
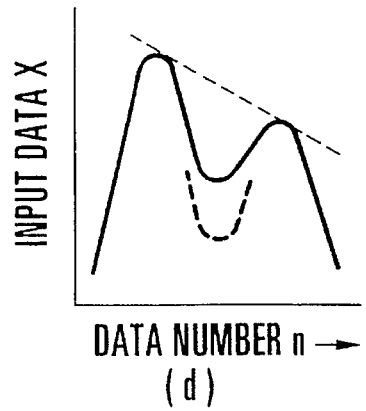
Figure 14E:
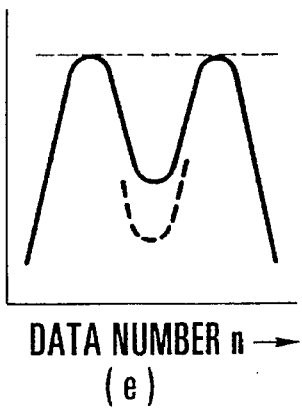
Figure 14F:
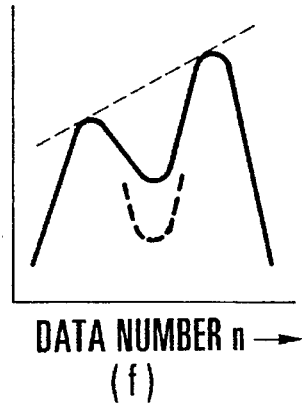
Figure 14G:
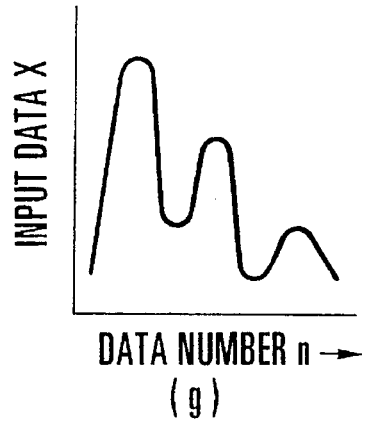
Figure 14H:
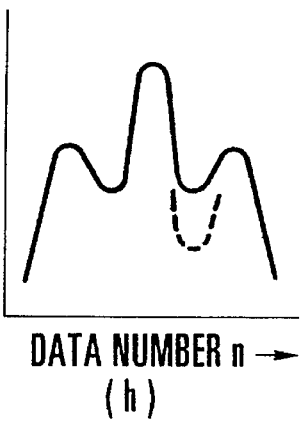
Figure 14I:
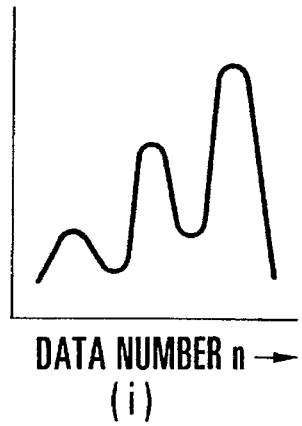

A further embodiment of the present invention is explained with reference to FIGS. 14A to 14I which illustrate the classification of the learning data. An abscissa represents an input data number n of the same case and an ordinate represents a magnitude of corresponding input data x. A number of examples are classified based on characteristics thereof as shown in FIGS. 14A to 14I. In FIGS. 14A to 14C, there is one peak, and they may be classified in detail based on the magnitude of peak, the value n for the peak and a partial gradient (convex upwardly or concave downwardly) although it is not shown. In FIGS. 14D to 14F, there are two peaks, and they may be classified based on the magnitudes of the left and right peaks, the magnitudes of the peaks and valleys, and the value n for the peak or valley (whether the n for the valley is closer to the n for the left peak or the n for the right peak) although it is not shown. In FIGS. 14G to 14I, there are three peaks and they may be classified from various aspects as described above. The classification may also be made based on shapes such as rectangular and pedestal although it is not shown.

The entire input data for learning is classified in accordance with FIGS. 14A to 14I, and a configuration of a multi-layer neural network and coupling weights among the neurons may be analytically determined in accordance with the above method. In the above analytical method, the configuration of the neural network and the coupling weights among the neurons are normally determined in several to several tens of seconds although it depends on the scale of data. Since the number of cases belonging to a particular class is smaller than that when no classification is made, the comparison is facilitated in the diagnosis and the discrimination of confusing and similar data is relatively easy, and the precision of diagnosis is improved. When the iterative learning method which requires a number of times of learning by the prior art back propagation learning method is learned after such classification, the time required to learn about all types may increases many times over. Accordingly, it is generally difficult to apply the present method to back propagation learning method after the classification of the input data. However, depending on the input data, it may be utilized for the back propagation learning method to reduce the overall learning time.

A further embodiment of the present invention is explained with reference to FIGS. 15 and 16. In the present embodiment, the analytical method explained in FIGS. 2 to 13 is expanded with the consideration of the scatter of the input data.

Figure 15:
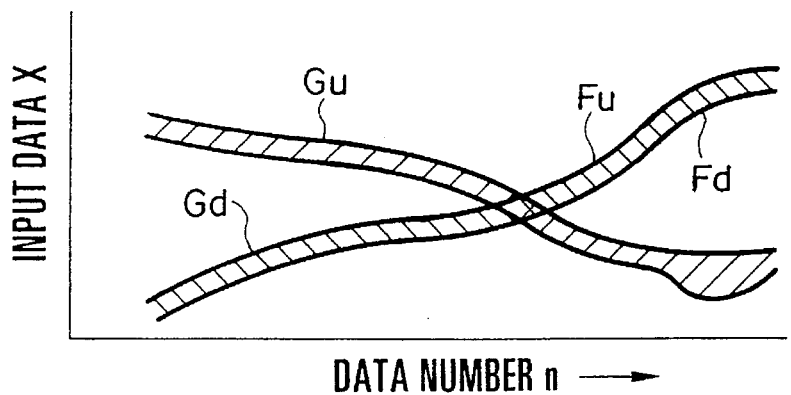
FIG. 15 shows learning data with consideration to a scatter.

In FIG. 15, an abscissa represents an input data number n and an ordinate represents a value x of the input, as they do in FIGS. 14A to 14I. Two measured curves F and G with scatter are shown. An upper limit of F is represented by $F_u$, a lower limit by $F_d$, an upper limit of G by $G_u$ and a lower limit by $G_d$.

In the explanation of the present invention, it is assumed that the input x is any positive value, the number of output (teacher data) of the neural network is 1, and the value thereof is "0" or "1". Where there is more than one output, each output is handled as follows.

It is assumed that when F is input, the neural network outputs "0", and when G is input, it outputs "1".

Total sums of inputs $Sf_u$, $Sf_d$, $Sg_u$ and $Sg_d$ excluding the threshold modifying input with arbitrarily determined weights (coupling weights) $K_i$ are determined by formula (11) as they $$Sf_u = \sum_{i=1}^{n} F_{ui} \cdot K_i$$
$$Sf_d = \sum_{i=1}^{n} F_{di} \cdot K_i$$
$$Sg_u = \sum_{i=1}^{n} G_{ui} \cdot K_i$$
$$Sg_d = \sum_{i=1}^{n} G_{ui} \cdot K_i$$

(11)

are in Table 1.

TABLE 5

Input Total Sums and Teacher Data Rearranged in the Order of Magnitude

| Case No. | Total Input Sum | Teacher Data | Remark |
| --- | --- | --- | --- |
| 1' | $Sf_u$ | 0 | Substitute by $S_1$ |
| 2' | $Sf_d$ | 0 | Substitute by $S_2$ |
| 3' | $Sg_u$ | 1 | Substitute by $S_3$ |
| 4' | $Sg_d$ | 1 | substitute by $S_4$ |

As shown in Table 5, the data are rearranged in the order of magnitude and they are displayed together with the corresponding teacher data. After such rearrangement, it is necessary to change the weights (coupling weights) of the second hidden layer et seq of the neural network depending on whether the teacher data having the maximum input total sum is "0" or "1". For the input F and G having a scatter, in order to get a correct solution as an output of the neural network if it is within the range of scatter, it is necessary that either a formula (12) or a formula (13) is met when the weight (coupling weight) to the input is positive or "0".

$$Sf_u \geq Sf_d \geq Sg_u \geq Sg_d \quad (12)$$

$$Sg_u \geq Sg_d \geq Sf_u \geq Sf_d \quad (13)$$

Depending on the manner of change of a curve, the formula (12) or (13) may be met even if all weights (coupling weights) to the inputs x are selected to be equal. However, depending on the curve, the value of other curve (for example, $Sg_u$) may fall between sums of one curve (for example, $Sf_u$ and $Sf_d$). In order to assure that the magnitude relation of the formula (12) or (13) is positively met, the following methodology is used. First, as candidates for the weights (coupling weights) $K_i$ to be used, 0.0001, 0.001, 0.01, 0.1, 1.0, 10.0, 100.0, 1000.0, 10000.0 etc. are prepared, and the right side of the crosspoint of the curves F and G of FIG. 15 is weighted with very large weights (coupling weights) $K_i$ compared to the left side (for example, 10 to 100 times) so that the total sums of inputs multiplied by the weights (coupling weights) are emphasized on the right side of the crosspoint of the curves F and G and the magnitude relation of the formula (12) in which the sum for the curve F is larger is met.

On the other hand, if the left side of the crosspoint of the curves of FIG. 15 is weighted with very large weights (coupling weights) $K_i$ compared to the right side (for example, 10 to 100 times), the total sums of the inputs multiplied by the weights (coupling weights) are emphasized on the left side of the crosspoint of the curves F and G so that the magnitude relation of the formula (13) in which the sum of the curve G is larger is met.

A magnitude relation should not be such that a total sum determined by other curves falls between two total sums determined by one curve.

When the weight (coupling weight) is positive or "0" for the data in the range of scatter shown for the curve F, the sum of the products of the inputs x and the weights (coupling weights) $K_i$ is always between $Sf_u$ and $Sd_d$. Similarly, when the weight (coupling weight) is positive or "0" for the data in the range of scatter shown for the curve G, the sum of the products of the inputs x and the weights (coupling weights) $K_i$ is always between $Sg_u$ and $Sg_d$. Accordingly, as will be explained later, by selecting the weights (coupling weights) to meet the formula (12) or (13), the same output as that designated by the curves $F_u$ and $F_d$ is attained for the input x in the range of scatter of the curve F. Similarly, the same output as that designated by the curves G" and $G_d$ is attained for the input x in the range of scatter of the curve G.

For the purpose of simplification, it is assumed that the formula (12) is met, the output (teacher data) is "0" for the curve F and the output (teacher data) is "1" for the curve G.

In order to make it easy to process the formulas of the Table 5, the characters are substituted as follows.

$$Sf_u \to S_1, Sf_d \to S_1, Sg_u \to S_3, Sg_d \to S_4$$

Figure 16:
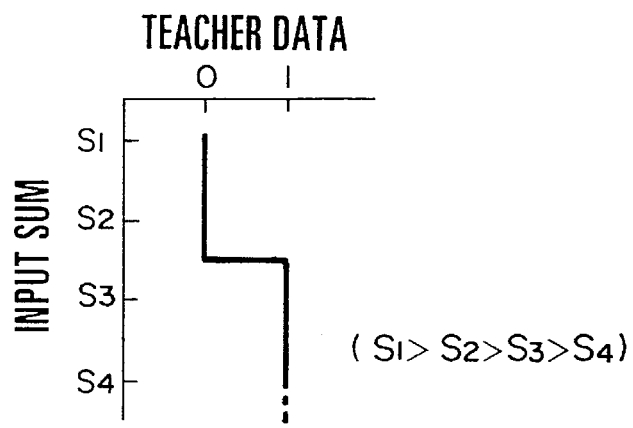
FIG. 16 shows a case in which teacher data changes one time.
Figure 17:
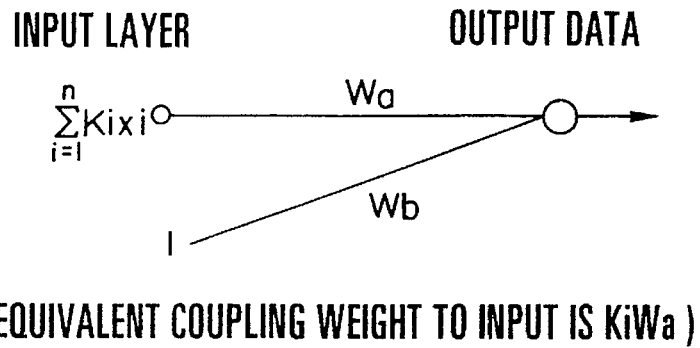
FIG. 17 shows a neural network in which teacher data changes one time.

In FIG. 16, an ordinate represents $S_1$, $S_2$, $S_3$ and $S_4$ of Table 5 and an abscissa represents the teacher data. The teacher data changes only once at the boundary of $S_2$ and $S_3$. In order to generate this simple change, no hidden layer is required in the neural network and a simple construction shown in FIG. 17 is sufficient. This is different from FIG. 5 in that the inputs are weighted. The coupling weights $W_a$ and $W_b$ of the neural network are determined as follows.

Based on the change of the teacher data of Table 5, the following simultaneous equations are prepared by using the input total sums $S_2$ and $S_3$ immediately before and after the boundary of change of the teacher data shown by broken lines in the Table while referencing to FIG. 17.

$$S_2 \cdot W_a + 1 \cdot W_b = -10 \quad (14)$$

$$S_3 \cdot W_a + 1 \cdot W_b = 10 \quad (15)$$

The value of the left term is the input to the output layer, and the value of the right term is an input value which allows that the output calculated by the formulas (1) and (2) be practically considered as "0" or "1".

(Because $1/(1+\exp(-(-10))) \approx 0$, $1/(1+\exp(-(10))) \approx 1$, see formulas (1) and (2))

By solving the above simultaneous equations ($S_2 - S_3 \neq 0$), $$W_a = -20/(S_2 - S_3) \quad (16)$$

$$W_b = 10 + 20S_3/(S_2 - S_3) \quad (17)$$

Since $W_a$ is negative and $W_b$ is positive, the following inequality is met if S' is smaller than $S_3$.

$$S' \cdot W_a + 1 \cdot W_b > 10 \quad (18)$$

Accordingly, the output to the input total sum which is smaller than $S_3$ of FIG. 16 is closer to "1" than that for $S_3$ and it may be practically considered as "1".

When S" is larger than $S_2$, the following inequality is met.

$$S'' \cdot W_a + 1 \cdot W_b < -10 \quad (19)$$

Accordingly, the output to the total input sum which is larger than $S_2$ of FIG. 17 is closer to "0" than that for $S_2$ and it may be practically considered as "0".

Thus, for the input in the range of scatter of the curve F or G of FIG. 15, "0" or "1" output is produced.

Figure 18:
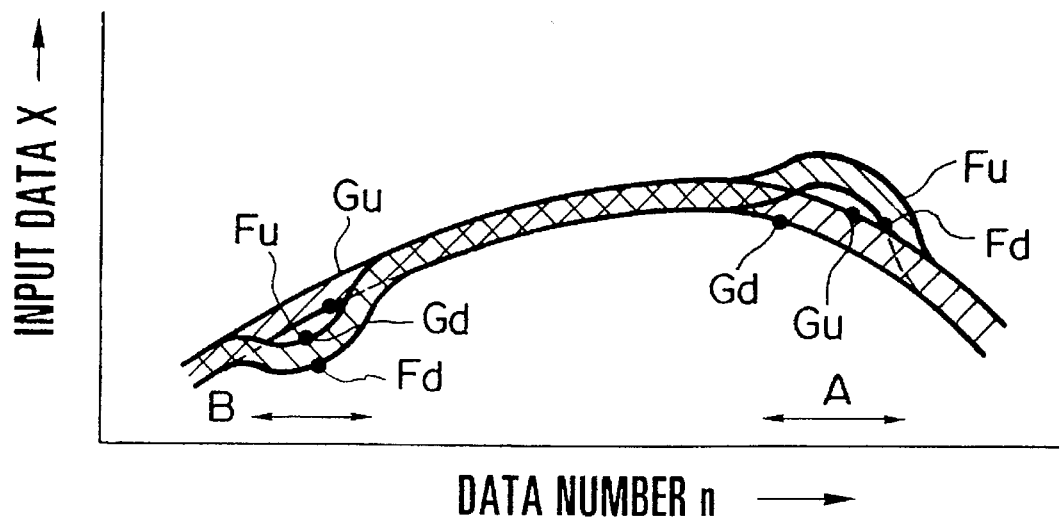
FIG. 18 shows learning data which mostly overlap.

FIG. 18 shows an example in which the curves F and G with scatter overlap in most areas. In such a case, if the weights (coupling weights) $K_i$ for the inputs are equal, the total sums of the inputs weighted by the coupling weights are almost equal depending on the shapes of the curves and the magnitude relation of the input total sums may not meet the above required relation.

However, if the weight (coupling weight) $K_i$ at one point in the non-overlapping area of the curves F and G is set sufficiently larger than the weights (coupling weights) $K_i$ of other area (for example, 10 to 100 times), the effect of the value of that area appears prominent so that the magnitude relation of the formula (12) or (13) is met. For example, if only the weight (coupling weight) $K_i$ in the range A of FIG. 18 is selected to be sufficiently large, the sum for the curve H becomes dominant and the formula (12) is met, and if only the coupling weight in the range B is selected to be sufficiently large, the sum for the curve G becomes dominant so that the formula (13) is met. If the weight $K_i$ in the range A is to be larger than those of other area and the weight $K_i$ in the range B is selected to be smaller than those of other areas, the curve F is more dominant. The opposite selection may be made.

Figure 19:
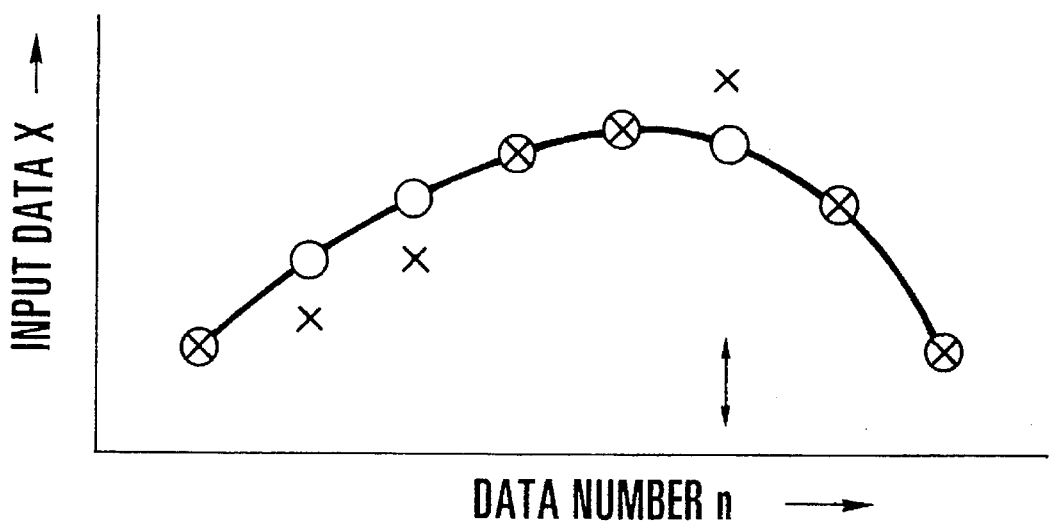
FIG. 19 shows learning data which mostly overlap.

FIG. 19 shows another approach for a similar case. In order to simplify the expression, the range of scatter is omitted in the drawing. In FIG. 19, again the abscissa represents the data number n and the ordinate represents the input data x. Two types of data are shown, one by circle and the other by X. Most data are overlapped but three data do not coincide to each other. Two data marked by X are smaller than the data marked by a circle and one data marked by X is larger than the data marked by a circle. In this case, if the scatter not shown is considered, the total sums of the products of the input data x and the weights (coupling factors) $K_i$ of the respective cases are almost equal if the weights (coupling factors) $K_i$ are simply made equal and the magnitude relation of the formula (12) or (13) may not be met. The approach to partially increase the coupling weights to the input data has been described above. In FIGS. 19–21, another method for meeting the magnitude relation of the formula (12) or (13) even if all coupling weights to the input data are equal is shown.

In FIG. 20, the data marked by X which is larger than the data marked with circle is not used as it is but the data marked by a circle and X for that data number n are used by reciprocals. The reciprocal of the data marked by a circle is represented by a dotted circle. The reciprocal of the data marked with X is represented by Δ. In the case classified by the mark X, two data marked with X and one data marked with Δ are smaller than the data marked by a circle (including a dotted circle) of the same data number. Accordingly, even if all weights (coupling weights) $K_i$ are selected to be equal, the total sum of the input marked with circle is larger and it can be discriminated.

In FIG. 21, the only one data marked by X which is larger than the data marked by a circle is left as it is, and the two inputs for the n marked with X which are smaller than the data marked with circle as well as the data marked with circle are used by reciprocals. As a result, two data marked by Δ and one data marked by X are larger than the data marked by a circle of the same data number. Accordingly, even if all weights (coupling weights) $K_i$ are selected to be equal, the total sum of the inputs marked by a circle is smaller and it can be discriminated.

Figure 22:
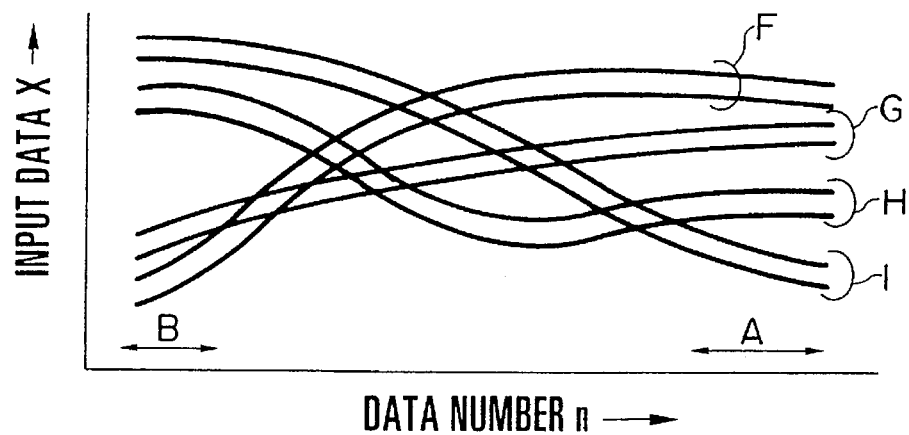
FIG. 22 shows data of four cases having scatter.

FIG. 22 shows four cases having scatter. In this case, a range of the data numbers such as a range A in which the data of the four cases assume different values from each other is selected, and the weights (coupling weights) $K_i$ for the input data in that range are selected sufficiently larger than those of other ranges. Thus, the total sums of the inputs weighted by the weights (coupling weights) $K_i$ are larger in the order of F, G, H and I, and the sum of the upper limits of the scatter of the data is smaller than the lower limit and the order of the total sums of the four cases is not disordered.

Figure 23:
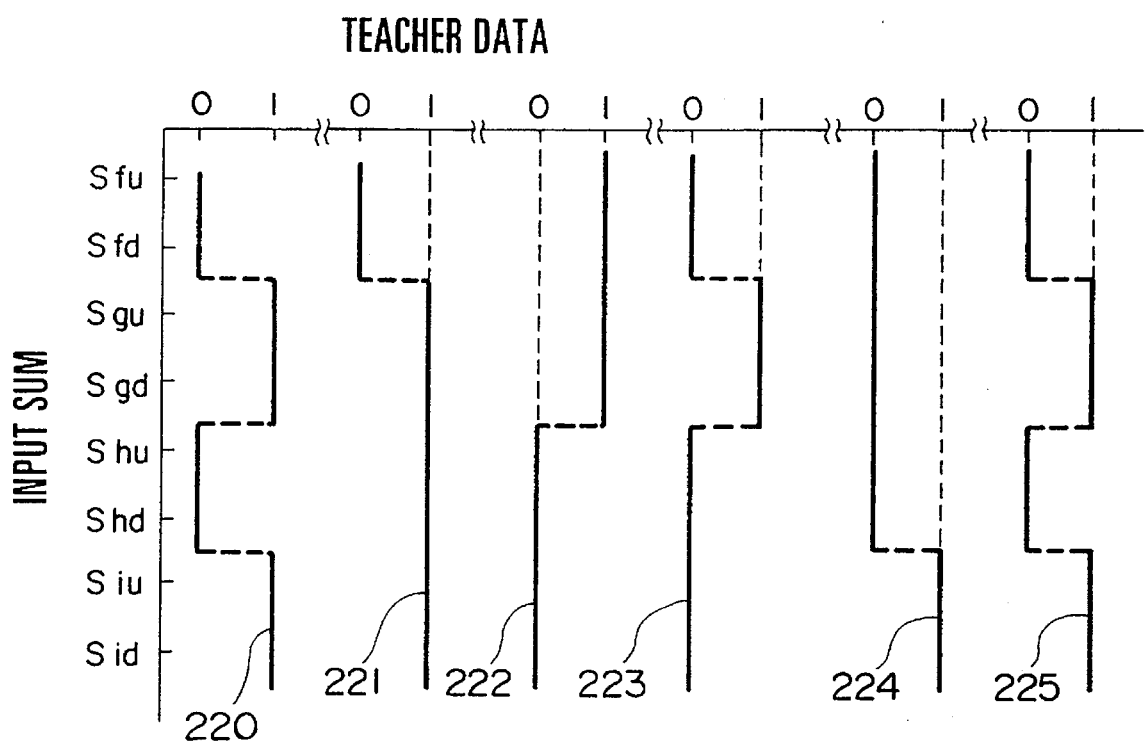
FIG. 23 shows a method (No. 1) of combination for teacher/data which changed three times.

Assuming that the output (teacher) data for the input data F, G, H and I are "0", "1", "0" and "1", the relation of the input total sums and the teacher data in the order of magnitude of the input total sum is shown in Table 6. The symbols for the input total sums are shown by $Sf_u$, $Sf_d$, $Sg_u$, $Sg_d$, $Sh_u$, $Sh_d$, $Si_u$, $Si_d$ with the suffixes u and d representing the upper limit and the power limit, respectively, as they do in the previous example. This relation may be represented by a segment graph as shown in FIG. 23.

As shown by a segment 220, the teacher data starts from 0, passes through 1 and returns again to 0 and finally becomes 1. The teacher data changes three times in this example. Segments 221 and 222 are generated in substantially the same manner as that of FIG. 4 and they are combined to generate a segment 223. Since the output may be "1" only when both of the segments 221 and 222 are "1", it is seen that they may be connected to an AND circuit. A segment 224 is generated in the same manner as that for the segment 221. Finally, the segments 223 and 224 are combined by an OR circuit. Since the output of the OR circuit is "1" when at least one of the inputs is "1", a segment 225 is generated. It coincides with the segment 220.

If the output (teacher) data for the input data F, G, H and I are reversed to "1", "0", "1" and "0", respectively, the relation between the input total sum and the teacher data is that shown in Table 7. This relation may be represented by a segment graph shown in FIG. 24. As shown by a segment 230, the teacher data starts from "1", passes through "0", returns again to "1" and finally becomes "0". The teacher data changes three times in this example. Since segments 231 and 232 are generated in the same manner as that of FIG. 4, the segments 231 and 232 are connected to an OR circuit to synthesize a segment 233. Then, a segment 234 is generated in the same manner as that for the segment 231. Finally, the segments 233 and 234 are combined in an AND circuit to generate a segment 235. It coincides with the segment 230.

In the above example, if the total sum of the products of the inputs and the weights (coupling weights) $K_i$ is between $Sf_u$ and $Sf_d$, between $Sg_u$ and $Sg_d$, between $Sh_u$ and $Sh_d$, or between $Si_u$ and $Si_d$, the output (teacher) data is designated. However, the output data is not designated when the total sum is between different curves, that is, between $Sf_d$ and $Sg_u$, between $Sg_d$ and $Sh_u$, or between $Sh_d$ and $Si_u$. In this case, the following process may be effected.

(a) Values of the both boundaries are output in accordance with a given formula.

(b) "?" is added in the output display to indicate non-inference.

As an example of (a), a value determined linearly or by a sigmoid function between "0" and "1" is output for a non-designated range between the output designations "0" and "1" in accordance with a deviation from the boundary.

Figure 24:
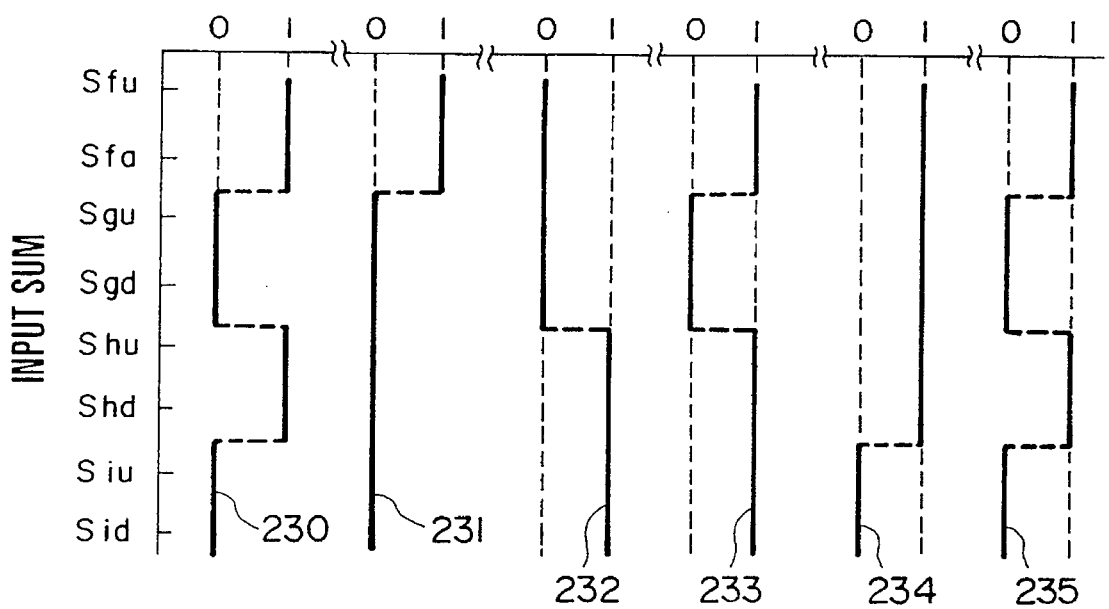
FIG. 24 shows a method (No. 2) of combination of teacher data which changes three times.
Figure 25:
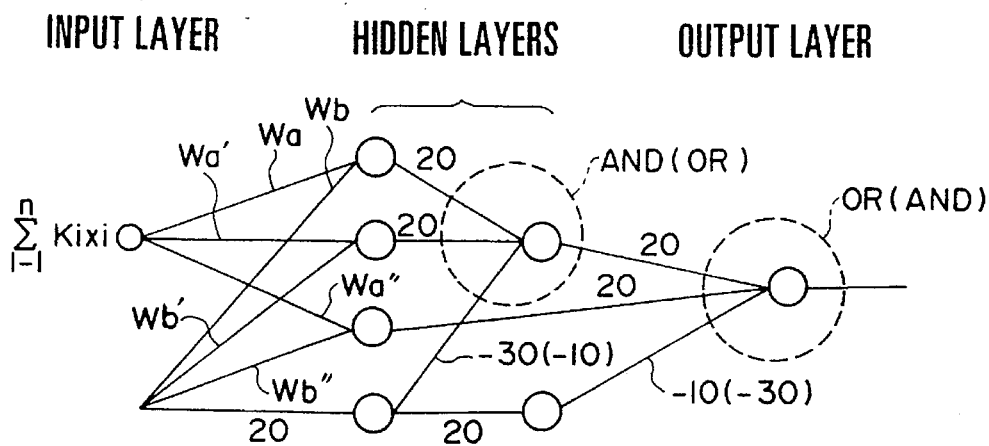
FIG. 25 shows a configuration of a neural network (in/ which teacher data changes three time)

FIG. 25 shows a configuration of the neural network corresponding to FIGS. 23 and 24. In a bottom line of the hidden layer, a neuron shown by hatching which always outputs "1" for modifying a threshold is coupled, and the input of the first hidden layer is coupled to only the threshold modifying input "1".

When the total sum of the inputs weighted by the weights (coupling factors) $K_i$ corresponds to the teacher data "0" as shown in FIG. 23, it is required that the second hidden layer functions as the AND circuit and the output layer functions as the OR circuit. On the other hand, when the maximum total sum of the inputs weighted by the weights (coupling weights) $K_i$ corresponds to the teacher data "1" as shown in FIG. 24, it is required that the second hidden layer functions as the OR circuit and the output layer functions as the AND circuit.

As seen from the those figures, only the coupling weight for modifying the threshold changes between the AND circuit and the OR circuit. An equivalent coupling weight to the input x is a product of the weight (coupling weight) $K_i$ used in the formula (11) and the coupling weights Wa and Wb determined by the formulas (16) and (17).

TABLE 6

Four input cases in which teacher data starts from 0

| Case No. | Input Total Sum | Teacher Data |
| --- | --- | --- |
| 1' | $Sf_u$ | 0 |
|  | $Sf_d$ | 0 |
| 2' | $Sg_u$ | 1 |
|  | $Sg_d$ | 1 |
| 3' | $Sh_u$ | 0 |
|  | $Sh_d$ | 0 |
| 4' | $Si_u$ | 1 |
|  | $Si_d$ | 1 |

TABLE 7

Four input cases in which teacher data starts from 1

| Case No. | Input Total Sum | Teacher Data |
| --- | --- | --- |
| 1' | $Sf_u$ | 1 |
|  | $Sf_d$ | 1 |
| 2' | $Sg_u$ | 0 |
|  | $Sg_d$ | 0 |
| 3' | $Sh_u$ | 1 |
|  | $Sh_d$ | 1 |
| 4' | $Si_u$ | 0 |
|  | $Si_d$ | 0 |

The present invention is also applicable to cases similar to Tables 6 and 7 where the teacher data changes in a more complex and more frequent manner.

Figure 26:
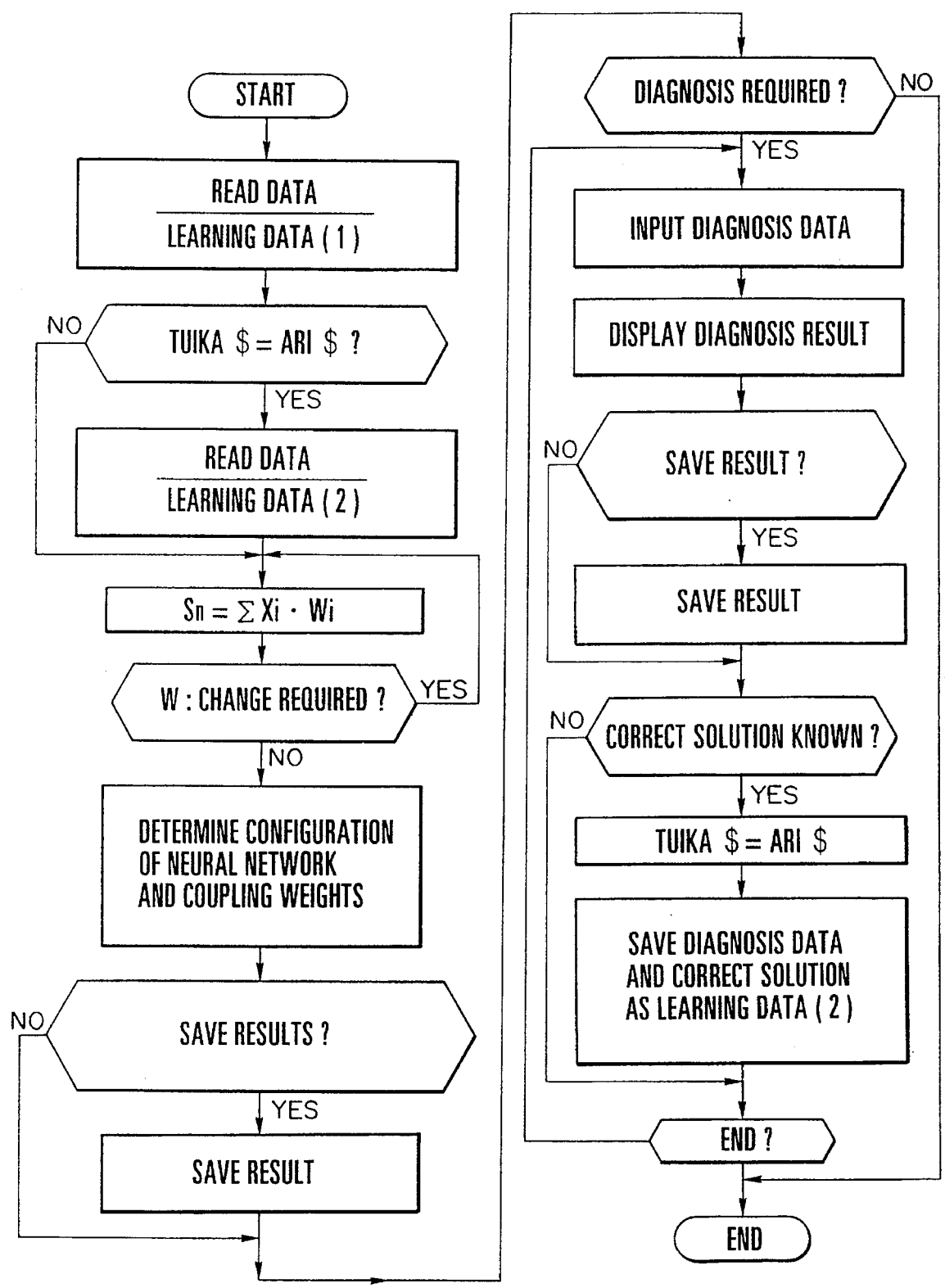
FIG. 26 shows a method for taking diagnosis data and correct solution therefor into leaning data.

Another embodiment which is applicable when a correct solution is known as the output for the diagnosis data is now explained with reference to a flow chart of FIG. 26.

When the calculation is started, learning data, teacher data therefor and a number of values which are candidates for the weights (coupling weights) $K_i$ are read as learning data (1) from a memory, a hard disk (HD) or a flexible disk (FD) of a computer.

Then, whether data to be added as the leaning data (2) is present or not is determined. Since there is no additional data initially (TUIKA$=NASHI$), the calculation of a total sum is initiated. Total sums of inputs weighted by appropriate weights (coupling factors) $K_i$ in the manner described above are determined and they are arranged together with the corresponding teacher data in the order of magnitude of the input total sum, and the number of times of change of the teacher data is considered. An output layer comprising the number of neurons of the first and second hidden layers determined by the number of times of change of the teacher data plus one neuron is prepared and the coupling weights are determined in the manner described above. In this step, the step corresponding to the learning in the prior art reverse propagation learning method is completed.

Then, a screen of a CRT (cathode ray tube) inquires the need for diagnosis. If Y (YES) is entered and the diagnosis data is input, the corresponding values are read from the memory, hard disk (HD) or flexible disk (FD) of the computer. Then, they are diagnosed and the result is displayed. Then, if Y is entered to the inquiry "Correct solution known?" on the CRT, the characters TUIKA$ are changed to ARI$ and the correct solution as well as the data input for the diagnosis are saved in the HD or FD as the learning data (2). Then, if Y is entered to the inquiry "Terminate?" on the CRT screen, the diagnosis is terminated.

While not shown, when the configuration of the neural network and the coupling weights have been determined, various values including the coupling weights may be saved in the HD or FD and necessary calculation loop may be modified for use in the next diagnosis to improve the efficiency.

When the calculation is resumed in the next run, the calculation is executed in substantially the same manner. As to the data diagnosed in the previous run and for which the correct solution has been input, it is added to the input data in the step of the learning data (2) so that the learning is done better and the correct solution is naturally given to the same inquiry as that of the diagnosis data correctly solved in the previous run. In this manner, the precision of diagnosis is enhanced gradually. In the present system in which the configuration of the neural network and the coupling weights are analytically determined, the diagnosis may be resumed with a higher precision in several to several tens of seconds after the addition of the learning data, although it depends on the scale of the number of data.

Table 8 show various propositions used in general inference.

TABLE 8

(1) If A, then B
(2) If not B, then not A
(3) If B, then A

For the proposition (1) of Table 8, the proposition (2) of Table 8 is referred to as a contraposition which is a proposition which uses the negation of a conclusion for one proposition as a hypothesis and the negation of the hypothesis as a conclusion. The true and false of the original proposition and the contraposition always match. On the other hand, the proposition (3) of Table 8 is referred to as a converse to (1). The converse is a proposition derived by inverting the hypothesis and the conclusion of one proposition. Even if the original proposition is true, the converse is not always true.

In the prior art neural network, which of the input learning data the diagnosis data is similar to is determined depending on which of the previously learned output (teacher) data the output data at the time of input of the diagnosis data is similar to. As seen from the general description of Table 8, when (1) of Table 8 is "If the learning data is A, then the output data is B", the use of (2) of Table 8 is always true but the use of (3) of Table 8 is not always true, in a strict sense. (3) of Table 8 includes those whose conclusions are A if the hypothesis is B and those whose conclusions are not B. However, in the neural network, there is a case in which a conclusion which is not A but similar to A may be treated as A without problem.

Figure 27:
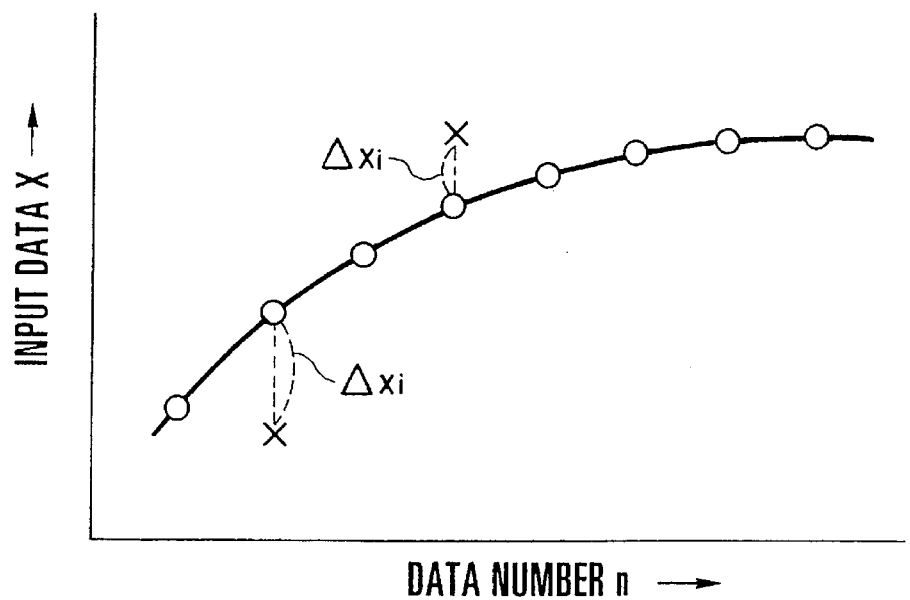
FIG. 27 shows learning data and diagnosis data.

An example is given. FIG. 27 shows input data of a neural network in one case. An abscissa represents a data number n and an ordinate represents input data x. The learning of data marked with circle in FIG. 27 corresponds to A of Table 8 (1) by a the output (teacher) data therefor corresponds to B of Table 8 (1). It is assumed that the diagnosis data are mostly equal to the data marked by a circle but only data numbers i and k are different. In FIG. 27, the data which coincide with the data marked by a circle are omitted for the expression of mark X. In the diagnosis data, the i-th and k-th data are represented by $(x_i+\Delta x_i)$ and $(x_k+\Delta x_k)$, and the weights (coupling weights) for the input data are represented by $K_i$ and $K_k$. A difference $\Delta S$ between total sums of the two inputs weighted by the weights (coupling weights) is given by:

$$\Delta S = \Delta x_i \cdot K_i + \Delta x_k \cdot K_k \quad (20)$$

If $K_i$ and $K_k$ have been set to appropriate values for the learning data marked with circle of FIG. 27, it is easy to give one of $\Delta x_i$ and $\Delta x_k$ to determine the other so that $\Delta S$ becomes zero. In this case, even if the learning has been made by using only the learning data marked by a circle and even if the data which is partially out of the range of the circle marks of FIG. 27 is diagnosed, the total sums weighted by the weights (coupling weights) are equal for the case of learning and the case of diagnosis, and hence the output data are equal for both cases. Namely, even if the output data are equal, the input data are not always equal. This corresponds to "the converse is not always true" as described in conjunction with Table 8. In this case, some are inferred from the output data as being anticipated and the others are non-anticipated ones. However, in the neural network, even if unlearned data is input, it may be regarded to be almost same as the learned data if the output is very similar to that for the learned data. In order to further enhance the precision of diagnosis, however, it is necessary to distinguish it from the output resulting in nonanticipated input data. A method for positively eliminating the nonanticipated data is explained with reference to FIG. 27.

The data for the diagnosis is input to calculate the output and most probable learning data is inferred from a number of learned cases. It is assumed that the data inferred to be most probable is the data marked by a circle in FIG. 27. Then, whether or not the data marked with circle in FIG. 27 matches to the diagnosis data is determined for each data number. If the learning data and the diagnosis data match each other for all of the input data, it is determined that the diagnosis data is equal to one for the selected learning case. If a portion of the input data does not match, it is determined that the diagnosis data is different from one for the selected leaning case. In this manner, the precision of diagnosis is enhanced.

When it is determined by the above diagnosis that the diagnosis data and the learning data do not completely match, "No match with learning data" may be indicated as well as "Similar cases" with a percentage of the number of matching data to the total number of inputs per case may be indicated. This will give a kinder reply to a user than simply indicating "No match with learning data".

In the above example, only two data do not match the data marked by a circle of FIG. 27. When more data do not match the data marked by a circle, a similar method may be applied.

Figure 28:
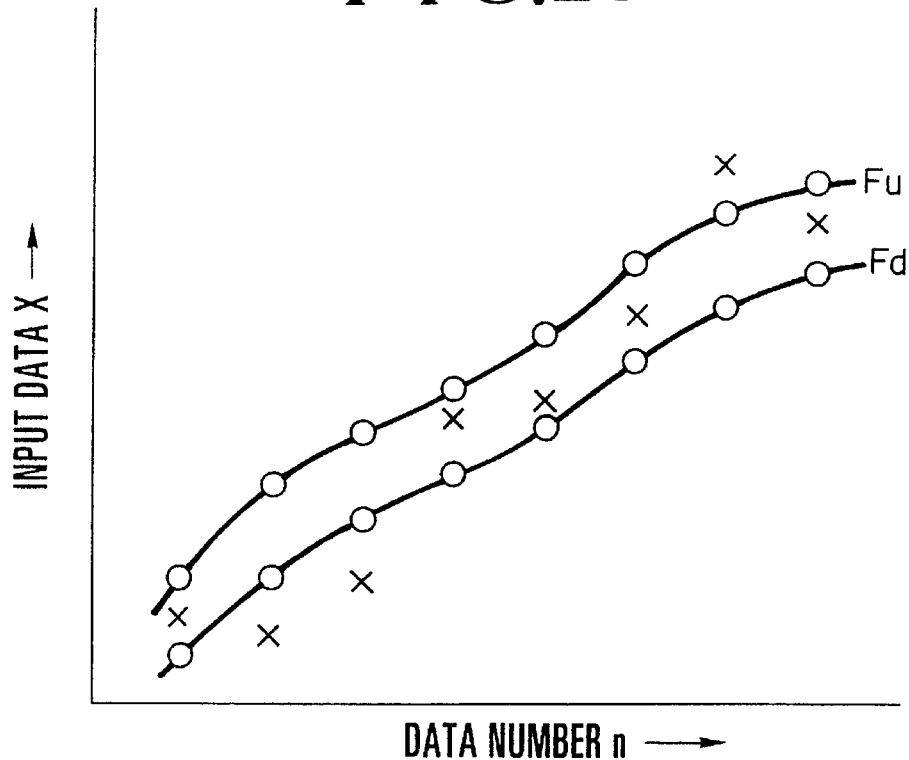
FIG. 28 shows learning data and diagnosis data with consideration to a scatter.

The confirmation of the diagnosis when the scatter of the learning data is taken into consideration is now explained with reference to FIG. 28. In FIG. 28, an abscissa represents the data number and an ordinate represents the input data. A curve $F_u$ shows upper limit input data of a curve F in one case, and a curve $F_d$ shows lower limit data of the same case. It is assumed that the curves $F_u$ and $F_d$ of FIG. 28 have been selected as the most probable case after the input of the diagnosis data and the calculation of the output. As in the case of FIG. 27, the following calculation for confirmation is made. Where $n_1$ is the number of input data per case;

(1) determine the number $n_2$ of diagnosis data (marked with X) which are on or below the curve $F_u$, and (2) determine the number $n_3$ of diagnosis data which are on or above the curve $F_d$.

If $n_1$, $n_2$ and $n_3$ are all equal, it is determined that the diagnosis data are in the range of the curves $F_u$ and $F_d$ and it corresponds to the case of the curve F.

If at least one of $n_2$ and $n_3$ is not equal to $n_1$, it is determined that a portion of the diagnosis data is out of the range of scatter encircled by the curves $F_u$ and $F_d$. In such a case, it is indicated that the diagnosis data do not completely match the learning data as well as the percentage of the diagnosis data to the input data which are between the curves $F_u$ and $F_d$ are indicated as explained in FIG. 27 so that the degree of similarity to the learning data is indicated for the convenience of the user. In this manner, exact diagnosis may be attained even for the input data having the scatter.

A specific method for comparing the diagnosis data and the learning data may be the following one instead of the steps (a) and (b) described above.

(a') Determine the number of diagnosis data which are above the curve $F_u$ of FIG. 28.

(b') Determine the number of diagnosis data which are below the curve $F_d$ of FIG. 28.

If both of the numbers of data determined in the steps (a') and (b') are zero, it is determined that the diagnosis data is within the range of scatter of the learned data for a case.

In FIG. 28, the upper limit $F_u$ and the lower limit $F_d$ of the range of scatter may be set somewhat larger than an actual scatter which may be experimentarily determined in order to prepare for any future possible expansion of the scatter for some reason. If the diagnosis data does not completely match to the learning data, not only the number of data which are out of the range of scatter but also the degree of deviation may be included to affect to the indication.

The methods described in FIGS. 27 and 28 may be applied to the following cases.

(1) Application to a reverse learning method of a multi-layer neural network (2) Application to the present invention to analytically determine the configuration of the multilayer neural network and the coupling weights.

(3) Not applied to the neural network but repeat the confirmation as described above as to the similarity of the diagnosis data to the learning data of all cases.

In any of the above cases, in order to compare the diagnosis data with the learning data, the respective numbers may be compared by prepared software, or a diagnosis data group and a learning data group of a case may be collectively compared by a matrix or a matrix formula to indicate a group having a value equal to or smaller than a value of another group, or count the number thereof.

The above cases (1) to (3) are explained in the reverse order of (3) to (1) for the convenience of explanation. In the method (3), to which learning case the diagnosis data is most similar (including totally match case) is determined for the input data of all cases. Accordingly, where the number of cases is large and the number of data per case is large, some time is required for the calculation for the diagnosis. However, in the prior art reverse propagation learning method, where the learning takes too much time or the learning does not proceed because of a local minimum, this method may be practiced if a high speed operation is not absolutely required. Since the correctness of diagnosis rather than the calculation speed is frequently required in the fault diagnosis, this method may be practical in many cases.

In the method (2), the diagnosis data is input, the output is calculated, the similar learning case is selected and the confirmation calculation is made in the manner described above. Since the number of times of calculation is smaller than that of the method (2), the calculation time is shorter and the diagnosis is more correct.

In the method (1), the confirmation calculation shown in FIGS. 27 and 28 is required in the worst case (where the configuration of the neural network is very simple, for example, the number of hidden layers is one and the number of neurons of the hidden layer is one). However, where the neural network is more complex, the confirmation calculation is possibly not required. This is explained below assuming that the number of hidden layer is one.

Where the number of neurons of the first hidden layer is more than one, the coupling weights between the neurons of the input layer and the first neuron of the first hidden layer are generally different from the coupling weights between the input layer and the second neuron of the first hidden layer. Accordingly, even if $\Delta S$ given by the formula (20) is zero with respect to the coupling weights between the input layer and the first neuron of the first hidden layer, $\Delta S'$ calculated in the same manner as that for $\Delta S$ with respect to the coupling weights between the input layer and the first hidden layer is highly possibly not zero. As a result, the output from the second neuron of the first hidden layer is very possibly different between the learning data and the diagnosis data. This effect generally also appears in the output of the output layer. As a result, the learning data marked by a circle shown in FIG. 27 and the diagnosis data (data which coincide with the circles are not shown) are highly probably discriminated. Where the configuration of the neural network is further complex, this trend is more prominent and the confirmation calculation described in connection with FIGS. 27 and 28 is not required in many cases.

Figure 29:
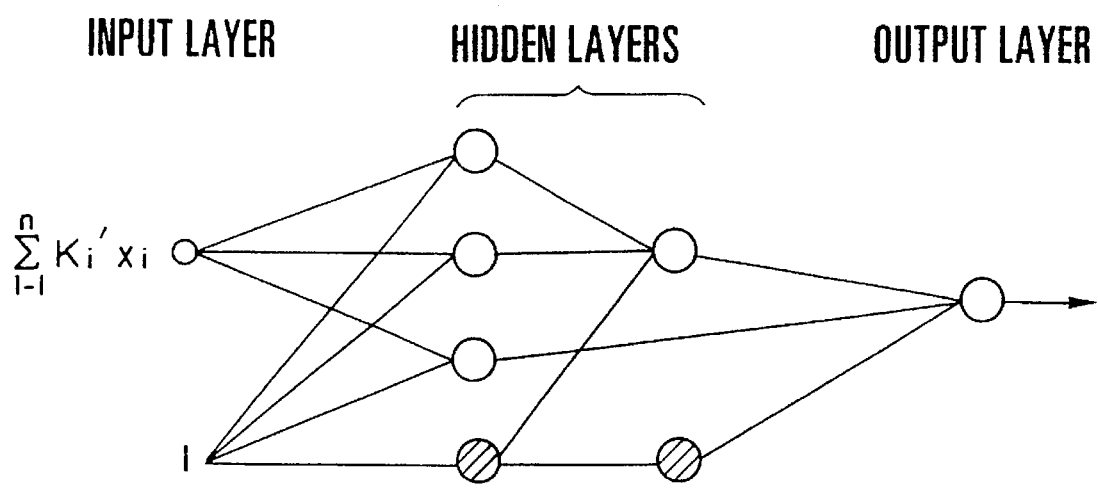
FIG. 29 shows coupling weights to an input in determining a second output.

In the analytical method of the present invention, it is naturally desired to eliminate the confirmation calculation in the diagnosis as much as possible. This may be attained to some extent where there are a plurality of outputs. This is explained in connection with the network of FIG. 25 and a network of FIG. 29 having a similar configuration. As to the first output, the configuration of the neural network and the coupling weights are determined by the method explained in connection with FIG. 25. Initial weights (coupling weights) for the input are shown by $K_i$. When the second output of FIG. 29 is to be determined, the initial weights (coupling weights) for the input are set differently from those for the first output within the range which meets the respective requirements explained in connection with FIG. 25, and they are shown by $K_i'$. Where other outputs are present, the initial coupling weights for the input are set differently from those of the first and second output calculations in a similar manner. Thus, even if a difference between the learning data and the diagnosis data does not appear in the first output shown in FIG. 25, a difference may most probably appear in the second output shown in FIG. 29 because the weights (coupling weights) to the input are changed. As a result, as a whole output data, the possibility of detection of difference between the learning data and the diagnosis data explained in FIG. 27 is increased.

In accordance with the present method, since the number of hidden layers and the number of neurons are known and the number of coupling weights to be learned is significantly decreased, the learning time can be reduced. Where a program of the reverse propagation learning is already present, the modification of the program is easy and various functions of the existing program can be utilized while the advantages of the present invention are retained.

By the methods described above, the equivalent status to that attained by the conventional iterative learning is attained in an efficient manner. Accordingly, by using the input data used for the calculation, the calculation output which is totally equal to or very close to the teacher data can be output. If the number of cases which are handled in this manner is set to be large, an output which is approximated to a similar input case can be output even for a totally new case. Accordingly, the present embodiment is applicable to various recognitions and diagnosis.

A comparison between the calculation by the present invention and the calculation by the conventional back propagation learning will be explained. The comparison was made by measuring corona noises of GIS in a known method, frequency analyzing the data stored in a flexible disk and reading representative data.

In the conventional back propagation learning method, the neural network shown in Table 9 was used. In order to determine a structure of a sample GIS, the number of outputs from the output layer was set to 3. It was intended to determine up to 8 (=2×2×2) types.

TABLE 9

| | |
|---|---|
| Number of input data per case | 10 |
| Number of outputs of output layer | 3 |
| Number of hidden layers | 1 |
| Number of neurons of hidden layer | 5 |
| Number of cases | 14 |

Three preferable outputs (teacher data) for each case are designated as shown in Table 10.

TABLE 10

| Case Number | Teacher Data | | |
|---|---|---|---|
| | Output 1 | Output 2 | Output 3 |
| 1 | 0 | 0 | 0 |
| 2 | 0 | 0 | 0 |
| 3 | 1 | 0 | 0 |
| 4 | 0 | 1 | 0 |
| 5 | 0 | 0 | 1 |
| 6 | 0 | 0 | 1 |
| 7 | 1 | 1 | 0 |
| 8 | 1 | 1 | 0 |
| 9 | 1 | 0 | 1 |
| 10 | 1 | 0 | 0 |
| 11 | 0 | 1 | 1 |
| 12 | 0 | 1 | 1 |
| 13 | 1 | 0 | 1 |
| 14 | 1 | 0 | 1 |

Outputs calculated by the conventional back propagation learning method are shown in Tables 11 and 12.

TABLE 11

| Case Number | After 400 times of learning | | | After 800 times of learning | | |
|---|---|---|---|---|---|---|
| | Output 1 | Output 2 | Output 3 | Output 1 | Output 2 | Output 3 |
| 1 | 0.000 | 0.562 | 0.398 | 0.000 | 0.478 | 0.504 |
| 2 | 0.042 | 0.431 | 0.392 | 0.000 | 0.133 | 0.508 |
| 3 | 0.922 | 0.018 | 0.575 | 1.000 | 0.115 | 0.160 |
| 4 | 0.000 | 0.966 | 0.548 | 0.000 | 1.000 | 0.267 |
| 5 | 0.071 | 0.163 | 0.461 | 0.000 | 0.000 | 1.000 |
| 6 | 0.098 | 0.166 | 1.000 | 0.002 | 0.000 | 1.000 |
| 7 | 0.957 | 0.208 | 0.486 | 1.000 | 0.956 | 0.000 |
| 8 | 0.951 | 1.000 | 0.272 | 1.000 | 1.000 | 0.000 |
| 9 | 1.000 | 0.200 | 0.394 | 0.965 | 0.000 | 0.980 |

TABLE 11-continued

| Case Number | After 400 times of learning | | | After 800 times of learning | | |
|---|---|---|---|---|---|---|
| | Output 1 | Output 2 | Output 3 | Output 1 | Output 2 | Output 3 |
| 10 | 0.975 | 0.131 | 0.452 | 1.000 | 0.046 | 0.136 |
| 11 | 0.000 | 0.981 | 1.000 | 0.000 | 1.000 | 1.000 |
| 12 | 0.000 | 0.552 | 0.398 | 0.000 | 0.507 | 0.465 |
| 13 | 0.996 | 0.020 | 0.972 | 0.973 | 0.009 | 1.000 |
| 14 | 0.970 | 0.031 | 0.964 | 0.980 | 0.019 | 1.000 |
| Calculation Time | 1 hour 47 minutes | | | 3 hours 34 minutes | | |
| Total Error | 1.259152 | | | 0.456008 | | |

TABLE 12

| Case Number | After 1200 times of learning | | |
|---|---|---|---|
| | Output 1 | Output 2 | Output 3 |
| 1 | 0.000 | 0.580 | 0.566 |
| 2 | 0.000 | 0.248 | 0.155 |
| 3 | 1.000 | 0.050 | 0.027 |
| 4 | 0.000 | 1.000 | 0.069 |
| 5 | 0.000 | 0.000 | 1.000 |
| 6 | 0.022 | 0.000 | 1.000 |
| 7 | 1.000 | 0.998 | 0.000 |
| 8 | 1.000 | 1.000 | 0.000 |
| 9 | 0.990 | 0.000 | 0.994 |
| 10 | 1.000 | 0.000 | 0.038 |
| 11 | 0.000 | 1.000 | 1.000 |
| 12 | 0.000 | 0.601 | 0.537 |
| 13 | 0.984 | 0.000 | 1.000 |
| 14 | 0.989 | 0.005 | 1.000 |
| Calculation Time | 5 hours 21 minutes | | |
| Total Error | 0.360491 | | |

In counting the number of times of learning, when the learning is completed one time for each case and all cases have been completed, it is counted as one time of learning. The numbers of times of learning are 400 and 800 in Table 11, and 1200 in Table 12. It is ideal that the calculation output completely matches to Table 10 but it does not completely match in the present example. Where "0" is expected as the output, the number no smaller than 0.5 is not permissible. Similarly, where "1" is expected as the output, the number smaller than 0.5 is not permissible. The impermissible numbers are underscored. As the number of times of learning increases from 400 to 800 and 1200, the number of underscored numbers decreases from 7 to 3 and 2. This shows that the calculation accuracy is enhanced. The times required for the calculation and the sums of the errors of the respective cases at the end of the calculation are also shown. In the present example, it is seen that five hours and twenty minutes are required for the 1200 times of learning and the decrease of the error is slow when the number of time of learning exceeds a certain number. The calculation of the back propagation learning is proceeded while the number of times of learning and the total error are displayed on the CRT. The total error does not decrease monotonously relative to the number of times of learning and it suddenly increases after decrease but gradually decreases as a general trend. In general, Table 12 is still insufficient for the required calculation precision and further learning is required.

Calculation result by the method of FIG. 2 of the present invention by using the same input data is shown in Table 13.

TABLE 13

| Case Number | Calculation Output | | |
|---|---|---|---|
| | Output 1 | Output 2 | Output 3 |
| 1 | 0 | 0 | 0 |
| 2 | 0 | 0 | 0 |
| 3 | 1 | 0 | 0 |
| 4 | 0 | 1 | 0 |
| 5 | 0 | 0 | 1 |
| 6 | 0 | 0 | 1 |
| 7 | 1 | 1 | 0 |
| 8 | 1 | 1 | 0 |
| 9 | 1 | 0 | 1 |
| 10 | 1 | 0 | 0 |
| 11 | 0 | 1 | 1 |
| 12 | 0 | 1 | 1 |
| 13 | 1 | 0 | 1 |
| 14 | 1 | 0 | 1 |
| Calculation Time | | 0.84 second | |
| Total Error | | 0.000 | |

As seen from Table 13, the calculation output rounded at fourth digit below a decimal point completely matches to the teacher data shown in Table 10. The time required for the calculation of the coupling weights is 0.84 second.

In the method of the present invention, since the analytical calculation is made and the iterative calculation to converge the number is not included, the calculation time is very short.

The present embodiment offers the following advantages:

(1) The number of hidden layers of the neural network and the number of neurons thereof can be determined based on the input data and the teacher data, and the coupling weights can be analytically calculated. Accordingly, the prior art reverse propagation iterative learning which requires a long time is not necessary and the time from the data input to the recognition and diagnosis can be reduced.

(2) Some time of trial and error required in the prior art method to select the number of hidden layers and the number of neurons thereof is not necessary. Accordingly, the calculation can be processed efficiently.

(3) It is applicable to a large scale neural network having a large number of input data and teacher data.

(4) Where the input data is added together with the teacher data, whether or it is worth for adding can be determined, and if it is determined to not be worthwhile, the addition can be cancelled to save the memory space of the computer.

(5) Since the iterative learning is not necessary, the calculation of the coupling weights between neuron to the diagnosis can be done by a more economic computer such as a notebook personal computer.

(6) Where the teachings of the present invention are applied to the neural network which requires the conventional back propagation method, the time required for the learning is significantly reduced because the number of hidden layers and the number of neurons are known, the relation between the coupling weights are known and the number of coupling weights which actually require the learning is very small, and the functions of the conventional program can be utilized as they are.

(7) Where the number of case of input data is large, they are classified into a plurality of classes based on some features of the cases and the learning and diagnosis are made for each class. Accordingly, the precision of diagnosis is enhanced even for similar or confusing cases.

(8) A correct solution is attained for the input data having a scatter if the scatter is within the predetermined range of scatter.

(9) A good method for selecting the coupling weights of the initial stage to classify the input data is provided and a selection efficiency is enhanced.

(10) In classifying the input data, a portion of data is not used directly but reciprocals thereof are used so that the input data can be efficiently classified.

(11) For the unlearned data, it may be inferred from the relation with adjacent data as it is done in the prior art, or the case of data not learned may be indicated by an appropriate expression such as "?" or a deviation from the learned data may be indicated so that more correct diagnosis is attained.

(12) Where there is teacher data which is a correct solution to the diagnosed input data, the diagnosed input data and the correct solution teacher data are efficiently added to the learning data. Accordingly, the precision of diagnosis is enhanced.

(13) The diagnosis data is input, the output is calculated and the most similar learning case is precisely inferred based on the output in a logically correct manner.

While the above description is primarily based on a method, the present invention may be implemented by hardware having a similar function. The fields of application of the present invention are not only engineering fields but also biotechnology and medical fields as well as the recognition and diagnosis of physical, chemical and biological phenomena and the recognition and diagnosis in agricultural, educational, economical and other various fields.

In accordance with the present invention, the coupling weights can be precisely and readily determined in a system such as the neural network, and the number of hidden layers and the number of neurons can be readily determined.

What is claimed is:

1. A method for analytically determining coupling weights using a neural network having an input layer, at least a hidden layer and an output layer, said method comprising the steps of:

classifying learning data input to said input layer based on features thereof into classifications of learning data;

inputting learning data for each of said classifications of learning data;

calculating a total sum for each of said classifications of learning data;

correlating teacher data corresponding to the calculated total sum for each of said classifications of learning data in the order of magnitude of the calculated total sum for each output of said output layer; and determining coupling weights based on the teacher data corresponding to the classification of learning data having a maximum calculated total sum, total sums of said classifications of learning data before and after any change of the teacher data, and the teacher data; and performing recognition or diagnosis by using said neural network having the determined coupling weights.

2. A method for analytically determining coupling weights using a neural network having an input layer, at least a hidden layer and an output layer, said method comprising the steps of:

inputting input data for each value for each classification of learning data based on an upper limit and a lower limit thereof to said input layer;

calculating a total sum for each of said classifications of learning data;

correlating teacher data corresponding to the calculated total sum for each of said classifications of learning data in the order of magnitude of the calculated total sum for each output of said output layer; and determining coupling weights based on the teacher data corresponding to the classification of learning data having a maximum calculated total sum, total sums of said classifications of learning data before and after any change of the teacher data, and the teacher data; and performing recognition or diagnosis by using said neural network having the determined coupling weights.

3. A method according to claim 2, wherein the input data input to said input layer are products of the upper limit and the lower limit multiplied by a same coupling weight.

4. A method according to claim 1 wherein two hidden layers are provided and the coupling weights are selected such that when the teacher data corresponding to the classification of learning data having the maximum total sum is 0, the second hidden layer functions as an AND circuit and said output layer functions as an OR circuit.

5. A method according to claim 1, wherein two hidden layers are provided and the coupling weights are selected such that when the teacher data corresponding to the classification of learning data having the maximum total sum is 1, the second hidden layer functions as an OR circuit and said output layer functions as an AND circuit.

6. A method according to claim 1, wherein said teacher data are used by reciprocals thereof for each classification of learning data and a reversal operation in the magnitude of the input data is executed.

7. A method according to claim 1 wherein a back propagation iterative learning method is used to calculate the coupling weights which are principal parts of the neural network.

8. A method for analytically determining coupling weights using a neural network having an input layer, at least a hidden layer and an output layer, said method comprising the steps of:

selecting coupling weights such that an input sum determined for a classification of learning data other than a particular classification of learning data input to said input layer does not fall between two input sums determined based on an upper limit and a lower limit of input data of said particular classification of learning data, and determining the input sum;

inputting said input sum as input data;

calculating an input sum for each classification of learning data;

calculating a total sum for each classification of learning data;

correlating teacher data corresponding to the input sum for each classification of learning data in the order of magnitude of the calculated total sum for each output of said output layer; and determining coupling weights based on the teacher data corresponding to the classification of learning data having a maximum total sum, total sums of classifications of learning data before and after any change of the teacher data, and the teacher data; and performing recognition or diagnosis by using said neural network having the determined coupling weights.

9. A method according to claim 8, wherein the teacher data of said particular classification of learning data and the teacher data of a classification of learning data other than said particular classification of learning data are different from each other.

10. A recognition or diagnosis method using a neural network having an input layer, at least a hidden layer and an output layer, said method comprising the steps of:

inputting learning data to said input layer for each classification of learning data;

calculating a total sum for each classification of learning data;

correlating teacher data to the calculated total sum for each classification of learning data in the order of magnitude of the calculated total sum for each output of said output layer;

determining coupling weights based on the teacher data corresponding to the classification of learning data having a maximum calculated total sum, total sums of said classifications of learning data before and after the change of the teacher data, and the teacher data; and indicating the deviation from a specified range of scatter of the learning data when input diagnosis data is out of the specified range; and performing recognition or diagnosis by using said neural network having the determined coupling weights.

11. A recognition or diagnosis method using a neural network having an input layer, at least a hidden layer and an output layer said method comprising the steps of:

inputting learning data to said input layer for each classification of learning data;

calculating a total sum for each classification of learning data;

correlating teacher data corresponding to the calculated total sum for each classification of learning data in the order of magnitude of the calculated total sum for each output of said output layer;

determining coupling weights based on the teacher data corresponding to the classification of learning data having a maximum calculated total sum, total sums before and after the change of the teacher data and the teacher data; and transferring diagnosis data and a corresponding correct solution as a portion of the learning data after the diagnosis when the correct solution to diagnosis data is known; and performing recognition or diagnosis by using said neural network having the determined coupling weights.

12. A recognition or diagnosis method using a neural network having an input layer, at least a hidden layer and an output layer, said method comprising the steps of:

inputting learning data to said input layer for each classification of learning data;

calculating a total sum for each classification of learning data;

correlating teacher data corresponding to the calculated total sum for each classification of learning data in the order of magnitude of the calculated total sum for each output of said output layer;

determining coupling weights based on the teacher data corresponding to the classification of learning data having a maximum calculated total sum, total sums before and after the change of the teacher data, and the teacher data; and calculating an output for diagnosis data when the diagnosis data is input;

inferring at least one probable learning data from the output corresponding to the diagnosis data;

comparing the diagnosis data with the learning data; and indicating the result of said comparing step.

13. A recognition or diagnosis method according to claim 12, wherein said inferred probable learning data includes a scatter, and the diagnosis data is compared with the learning data having the scatter and the result thereof is indicated.

14. A recognition or diagnosis method according to claim 12 wherein a first coupling weight to be multiplied to the input data of said input layer is selected to be different from other coupling weights.

15. A recognition or diagnosis method, comprising the steps of:

classifying learning data input to an input layer based on characteristics thereof;

inputting learning data for each classification of learning data;

calculating a total sum for each classification of learning data;

correlating teacher data corresponding to the calculated total sum for each classification of learning data in order of magnitude of the calculated total sum for each output of said input layer;

determining coupling weights based on the teacher data corresponding to the classification of learning data having a maximum calculated total sum, total sums before and after a change of the teacher data, and the teach data;

comparing diagnosis data directly with learning data;

determining whether the diagnosis data and the learning data of a particular classification of learning data totally match, partially match or totally mismatch; and indicating the result if said determining step.

16. A diagnosis evolution method, comprising the steps of:

comparing diagnosis data directly with learning data having a range of scatter;

determining whether the diagnosis data is totally within said range, partially within said range or totally out of said range; and indicating the result of said determining step.

17. A recognition or diagnosis method, comprising the steps of:

classifying learning data input to an input layer based on characteristics thereof;

inputting learning data for each classification of learning data;

calculating a total sum for each classification of learning data;

correlating teacher data corresponding to the calculated total sum for each classification of learning data in order of magnitude of the calculated total sum for each output of said input layer;

determining coupling weights based on the teacher data corresponding to the classification of learning data having a maximum calculated total sum, total sums before and after a change of the teacher data, and the teach data;

preparing simultaneous equations by using calculation formulas of inputs to a neuron based on an upper limit and a lower limit of input data having a range of scatter;

solving the simultaneous equations to determine coupling weights; and performing recognition or diagnosis by using said neural network having the determined coupling weights.

18. An apparatus for diagnosing an electrical circuit to be used under a plurality of conditions by using a neural network comprising;

means for utilizing the plurality of conditions as learning data to determine coupling weights which form said neural network;

means for classifying learning data input to an input layer based on characteristics thereof;

means for inputting learning data for each classification of learning data;

means for calculating a total sum for each classification of learning data;

means for correlating teacher data corresponding to the calculated total sum for each classification of learning data in order of magnitude of the calculated total sum for each output of said input layer; and means for determining coupling weights based on the teacher data corresponding to the classification of learning data having a maximum calculated total sum, total sums before and after a change of the teacher data, and the teach data; and means for performing recognition or diagnosis by using said neural network having the determined coupling weights.

* * * * *